(12) United States Patent
Nakashima et al.

(10) Patent No.: US 9,597,360 B2
(45) Date of Patent: Mar. 21, 2017

(54) METHOD OF TREATMENT FOR PULPITIS AND/OR ENHANCEMENT FOR DENTINOGENESIS

(71) Applicant: National Center for Geriatrics and Gerontology, Obu-shi, Aichi (JP)

(72) Inventors: Misako Nakashima, Obu (JP); Hiroshi Nakamura, Nagoya (JP)

(73) Assignee: NATIONAL CENTER FOR GERIATRICS AND GERONTOLOGY, Obu-Shi, Aichi (JP)

( * ) Notice: Subject to any disclaimer, the term of this patent is extended or adjusted under 35 U.S.C. 154(b) by 0 days.

(21) Appl. No.: 14/866,598

(22) Filed: Sep. 25, 2015

(65) Prior Publication Data

US 2016/0008405 A1 Jan. 14, 2016

Related U.S. Application Data

(63) Continuation of application No. 12/936,474, filed as application No. PCT/JP2009/057410 on Apr. 6, 2009, now abandoned.

(30) Foreign Application Priority Data

Apr. 7, 2008 (JP) .................. 2008-099814

(51) Int. Cl.
| | | |
|---|---|---|
| *A61K 35/44* | (2015.01) | |
| *A61K 35/32* | (2015.01) | |
| *A61K 38/48* | (2006.01) | |
| *G01N 33/50* | (2006.01) | |
| *A61K 6/00* | (2006.01) | |
| *A61K 6/02* | (2006.01) | |
| *A61K 35/36* | (2015.01) | |

(52) U.S. Cl.
CPC ............ *A61K 35/32* (2013.01); *A61K 6/0017* (2013.01); *A61K 6/0067* (2013.01); *A61K 6/02* (2013.01); *A61K 35/36* (2013.01); *A61K 35/44* (2013.01); *A61K 38/4886* (2013.01); *G01N 33/5023* (2013.01); *G01N 33/5064* (2013.01); *G01N 33/5073* (2013.01); *G01N 2333/96494* (2013.01); *G01N 2800/18* (2013.01)

(58) Field of Classification Search
CPC .......................................... G01N 2333/96494
See application file for complete search history.

(56) References Cited

U.S. PATENT DOCUMENTS

| | | |
|---|---|---|
| 2003/0113812 A1 | 6/2003 | Hemperly |
| 2005/0079470 A1 | 4/2005 | Rutherford et al. |
| 2006/0115782 A1* | 6/2006 | Li .................... A61C 19/063 433/6 |
| 2007/0184083 A1 | 8/2007 | Coughlin |
| 2007/0248933 A1 | 10/2007 | Rutherford et al. |
| 2009/0148486 A1 | 6/2009 | Lu et al. |
| 2010/0203481 A1 | 8/2010 | Murray et al. |
| 2011/0002895 A1 | 1/2011 | Ueda et al. |
| 2011/0020310 A1 | 1/2011 | Nakashima et al. |
| 2011/0044960 A1 | 2/2011 | Nakashima et al. |

FOREIGN PATENT DOCUMENTS

| | | |
|---|---|---|
| EP | 2286829 A1 | 2/2011 |
| JP | 6-256132 | 9/1994 |
| JP | 2002-363084 A | 12/2002 |
| JP | 2004-67630 A | 3/2004 |
| JP | 2005-263681 A | 9/2005 |
| JP | 2006-211957 A | 8/2006 |
| WO | WO 01/63287 A1 | 8/2001 |
| WO | WO 2005/034789 A2 | 4/2005 |
| WO | WO 2006/032075 A1 | 3/2006 |
| WO | WO 2006/116530 A2 | 11/2006 |
| WO | WO 2009/072527 A1 | 6/2009 |
| WO | WO 2009/113733 A1 | 9/2009 |
| WO | WO 2009/125859 A1 | 10/2009 |

OTHER PUBLICATIONS

Jiang, L. et al. 2008 "Expression and role of SDF-1a-CXCR4 axis in human dental pulp" *J Endod* 34(8): 939-944.

Amano, K. et al., "MMPs regulate wound healing process in rat dental pulp," *Japanese Society of conservative Dentistry Magazine* Oct. 5, 2007, pp. 35.

Boukpessi, T. et al. 2008 "The effect of stromelysin-1 (MMP-3) on non-collagenous extracellular matrix proteins of demineralized dentin and the adhesive properties of restorative resins" *Biomaterials* 29: 4367-4373.

Corti, S. et al. 2005 "Multipotentiality, homing properties, and pyramidal neurogenesis of CNS-derived LeX(ssea-1)$^+$/CXCR4$^+$ stem cells" *The FASEB Journal* 19: 1860-1862.

Gotlieb, E.L. et al. 2008 "An ultrastructural investigation of tissue-engineered pulp construct implanted within endodontically treated teeth" *Journal of the American Dental Association* 139: 457-465.

Huang, G.T.-J, et al, 2009: "Stem/Progenitor Cell-Mediated De Novo Regeneration of Dental Pulp with Newly Deposited Continuous Layer of Dentin in an In Vivo Model", *Tissue Engineering*, 16(2): 605-615.

Iohara, K. et al. 2006 "Side population cells isolated from porcine dental pulp tissue with self-renewal and multipotency for dentinogenesis, chondrogenesis, adipogenesis, and neurogenesis" *Stem Cells* 24: 2493-2503.

(Continued)

*Primary Examiner* — Robert Yamasaki
*Assistant Examiner* — Teresa E Knight
(74) *Attorney, Agent, or Firm* — Knobbe, Martens, Olson & Bear, LLP

(57) ABSTRACT

A method of treatment for pulpitis and/or enhancement for dentinogenesis, includes using dental materials that include at least one of a protein having matrix metalloprotease 3 activities or matrix metalloprotease 3 precursor protein as an active ingredient. The dental materials can also contain a carrier having biocompatibility, and can contain at least one cell type among pulp cells, pulp stem cells, pulp progenitor cells, odontoblasts or cells that can differentiate into odontoblasts.

11 Claims, 24 Drawing Sheets

(56) References Cited

OTHER PUBLICATIONS

Iohara, Koichiro, et al., "CD31 negative SP cells derived from dental pulp accelerate vascularization and pulp regeneration," Japanese Society of conservative Dentistry Magazine, Oct. 5, 2007, p. 106.

Iohara, K. et al. 2008 "A novel stem cell source for vasculogenesis in ischemia: Subfraction of side population cells from dental pulp" Stem Cells 26: 2408-2418.

Iohara, K. et al. 2009 "Regeneration of dental pulp after pulpotomy by transplantation of CD31⁻/CD146⁻ side population cells from a canine tooth" Regenerative Medicine 4: 377-385.

Kawanishi, H.N. et al., "Effects of an inducible nitric oxide synthase inhibitor on experimentally induced rat pulpitis," European Journal of Oral Science 2004; 112; pp. 332-327.

Koblas, T. et al. 2007 "Isolation and Characterization of Human CXCR4-Positive Pancreatic Cells" Folia Biol (Praha) 53: 13-22.

Kucia, M et al. 2007 "Morphological and molecular characterization of novel population of CXCR4⁺SSEA-4⁺ Oct-4⁺ very small embryonic-like cells purified from human cord blood—preliminary report" Leukemia 21: 297-303.

Laureys, W. et al. 2001 "Revascularization after cryopreservation and autotransplantation of immature and mature apicoectomized teeth" American Journal of Orthodontics and Dentofacial Orthopedics 119: 346-352.

Moriguchi, M. et al. 1998 "Immunocytochemistry of proteoglycan in dentin and odontoblasts" Kaibogaku Zasshi-Acta Anatomica Nipponica 73: 239-245.

Murray, et al, 2007: "Regenerative Endodontics: A Review of Current Status and a Call for Action", Journal of Endodontics, Lippincottt Williams & Wilkins , 33(4): 377-390.

Nakagawa, K.-I. et al. 1984 "Histo-pathological Studies of Synthetic Hydroxyapatite Applied as Root Canal Filling Materials to Apical Wounds of Dog Teeth (Part 1)" The Japanese Journal of conservative Dentistry 27: 190-199.

Nakao, K. et al. 2008 "Dental regenerative therapy: stem cell transplantation and bioengineered tooth replacement" Japanese Dental Science Review 44: 70-75.

Nakashima, M. and Akamine, A. 2005 "The Application of Tissue Engineering to Regeneration of Pulp and Dentin in Endodontics" Journal of Endodontics 31: 711-718.

Nakashima, M. and Reddi, A.H. 2003 "The application of bone morphogenetic proteins to dental tissue engineering" Nature Biotechnology 21: 1025-1032.

Nakashima, M. 2007 "Tissue engineering of teeth" Handbook of Biomineralization 3 (Medical and Clinical Aspects): 265-281.

Nakashima, M, et al, 2009: "Human dental pulp stems with highly angiogenic and neurogenic potential for possible use in pulp regenartion", Cytokine & Growth Factor Reviews, 20(6): 435-440.

Soukup, T, et al, 2006: "Biological properties and flow cytometric analysis of human dental pulp stem cells", Cytotherapy, Isis Medical Media, 8(2): 3.

St. John Sutton, M. et al. 2000 "Left ventricular remodeling after myocardial infarction: pathophysiology and therapy" Circulation 101: 2981-2988.

Supplemental European Search Report for European Application No. EP 09 73 08939, dated Jan. 24, 2012.

Tsutsui, T. et al., "Acceleration of calcification by co-culture of epithelial cells derived from human gum and fibroblasts, and epithelial cells derived from human gum and dental pulp cells," Journal of Oral Biosciences vol. 47, Suppl. 2005, p. 155, 324 2P.

Tsutsui, T. et al., "Calcification under co-culture of pithelial cells and mesenchymal cells," Oral Tissue Culture Association Magazine, vol. 16 (1), 2007 pp. 11-12.

Yang, S et al. 2001 "The design of scaffolds for use in tissue engineering. Part I. Traditional factors" Tissue Engineering 7: 679-689.

Yoshiyama, M et al., "Seeking a New Caries Treatment: New Conversion from Restoration to Dentin Regeneration" Japan Association for Dental Science Magazine, vol. 22, 2003, pp. 76-80.

Zhang, W. et al. 2006 "The performance of human dental pulp stem cells on different three-dimensional scaffold materials" Biomaterials 27: 5658-5668.

* cited by examiner

500 μm

300 μm

50 μm

100 μm

100 μm

100 μm

100 μm

100 μm

100 μm

100 μm

150 μm 1, 4, 7: strong compression stimulation
2, 5, 8  weak compression stimulation
3, 6, 9  control    no compression stimulation

METHOD OF TREATMENT FOR PULPITIS AND/OR ENHANCEMENT FOR DENTINOGENESIS

TECHNICAL FIELD

The present invention relates to medicaments for treatment of pulpitis and/or enhancement of dentinogenesis, and specifically relates to utilization of matrix metalloproteinase 3 for injury and lost of pulp tissue and surrounding tissue.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SequenceListing.txt, the date of creation of the ASCII text file is Sep. 25, 2015, and the size of the ASCII text file is 4.91 KB.

BACKGROUND ART

When dental caries is deep enough to reach dental pulp in the treatment of caries, whole pulp removal (pulpectomy) and filling in the emptied root canal with root canal filler is usually performed for treatment of the caries. It is thought to be preferable to preserve the dental pulp tissue as long as possible due to disadvantage of pulpectomy (weakness in tensile strength of dentin, and further progression of secondary caries by the lost of sense). There are two treatment methods for preserve dental pulp tissue; direct pulp capping that covers the surface of exposed pulp, and pulpotomy that cover the amputated root pulp.

It is critical for these methods to induce dentin formation in the outer surface of the exposed pulp tissue in order to preserve dental pulp tissue. For this purpose, as described in Non-patent documents 1, 2 and 3, pulp capping reagent has been developed to enhance dentin formation.

It is also critical for these methods to suppress pulp inflammation and pain and enhance angiogenesis/vasculogenesis and pulp regeneration in order to conserve dental pulp tissue. For this purpose, as described in Non-patent Literature 1, pulp capping reagent has been developed to suppress pulp inflammation.

CITATION LIST

Patent Documents

PATENT DOCUMENT 1: Japanese Patent Publication Laid-Open No. 2002-363084
PATENT DOCUMENT 2: Japanese Patent Publication No. H6-256132
PATENT DOCUMENT 3: Japanese Patent Publication Laid-Open No. 2005-263681

Non-Patent Document

NON-PATENT DOCUMENT 1: Kawanishi H N, Kawashima N, et al., Effects of an iNOS inhibitor on experimentally induced rat pulpitis, Eur. J. Oral. Sci., 112, 332-337, 2004.

SUMMARY OF THE INVENTION

Technical Problem

However, the ability of these conventional pulp capping agents to accelerate dentin formation was not necessarily enough. In the pulp capping agent described in the patent document 1 a blood extract is used as an active ingredient. However, the potential to promote dentin formation is insufficient, and the pulp capping agent described in the patent document 1 has a problem from the viewpoint of safety. In addition, in the pulp capping agent described in the patent document 2, N-acetylglucosamine is used as an active ingredient. However, the pulp capping agent in the patent document 2 does not contain morphogens, cell growth/differentiation factors, and cell migration factors essential for induction of odontoblast differentiation, and only adsorbs a factor indirectly released from a local site without a required morphosis factor. Therefore the pulp capping agent in the patent document 2 is inadequate for acceleration of dentin formation and regeneration of dentin/pulp complex. The pulp capping agent in the patent document 3 contains a polyphosphoric acid as an active ingredient. However, the potential to stimulate dentin formation is insufficient. The pulp capping agent described in the non-patent document 1 contains an inhibitor for nitric oxide inducible enzyme as an active ingredient. The pulp capping agent described in the non-patent document 1 the anti-inflammatory effect to inhibit a nitric oxide inducible enzyme and destruct one end of the inflammatory mediator network. However, its effect on acceleration of vasculogenesis/angiogenesis and pulp regeneration is insufficient.

Therefore this invention is intended to provide medicaments for treatment of pulpitis and/or acceleration of dentin formation. In addition, this invention is intended to provide dental materials for treatment of pulpitis and/or acceleration of dentin formation. In addition, this invention is intended to provide the screening method for the active ingredient of the medicaments to treat pulpitis and/or accelerate dentin formation.

Solution to the Problem

The inventors have isolated some subfraction with high vasculogenic/angiogenic potential from SP cell fraction (CD31$^-$/CD146$^-$ SP cells) which enriched for dental pulp stem cells, and performed the gene expression profiling of this pulp SP cell subfraction. As a result, these inventors discovered that matrix metalloprotease 3 (MMP3), a degrading enzyme of the extracellular matrix implicated in the degradation of the extracellular matrix and the basement membrane, was highly expressed in this pulp SP cell subfraction. Furthermore, these inventors discovered that this protein is useful to enhance healing of the injured pulp, repair/regeneration of pulp/dentin and healing of pulpitis. These inventors completed this invention based on these findings. In other words, according to this invention, the following means is demonstrated.

The medicaments affecting the first view point of this invention is characterized by comprising at least one of a protein having matrix metalloprotease 3 activity or matrix metalloprotease 3 precursor protein as an active ingredient. The medicaments of this invention is useful for a medicine at the time of the injury of dental pulp or the partial loss. The medicaments of this invention is particularly useful to prevent or treat pulp-related diseases such as pulpitis or the periapical periodontisis.

It is preferable that the ratio of the active ingredient including at least one of a protein having matrix metalloprotease 3 activities or matrix metalloprotease 3 precursor protein is 12 ng/ml-1000 ng/ml.

The dental materials relating to the second view point of this invention are characterized by comprising at least one of a protein having matrix metalloprotease 3 activities or matrix metalloprotease 3 precursor protein as an active ingredient.

It is preferable for the above mentioned dental material to include a carrier having biocompatibility. This carrier is to be permitted pharmaceutically.

The above carrier is preferable to have at least on one side a plurality of recesses which depth and orientation direct to a constant course, and to be membranous structure consisting of materials having oxygen permeability and/or material permeability.

It is preferable for the above carrier to have at least one of collagen, artificial proteoglycan, glycosaminoglycan, gelatine, hydrogel, fibrin, phosphophoryn, hyaluronic acid, chitin, glucosamine, fibronectin, alginic acid, heparan sulfate, heparin, laminin, tricalcium phosphate, hydroxyapatitte, μ-TCP, polylactic acid, polyglycolic acid, poly-DL-lactic acid, lactic acid glycolic acid copolymer, polyethylene glycol, polysilicon, polycaprolactone, calcium carbonate, titanium, gold, ceramics, silicone resin or silicon hydrogel.

It is preferable for the dental material in this invention to have at least one of pulp cells, pulp stem cells, pulp progenitor cells, odontoblasts or cells that can differentiate into odontoblasts.

It is preferable for the cells having at least one of pulp cells, pulp stem cells, pulp progenitor cells, odontoblasts or cells that can differentiate into odontoblasts is more than $1\times10^3$ cells/μl and lower than $1\times10^6$ cells/μl.

It is preferable for the dental materials in this invention to further include endothelial cells or endothelial progenitor cells.

It is preferable for the dental materials in this invention to further include epithelium.

It is preferable for the dental materials of this invention to further include dentin matrix.

In addition, in dental materials in this invention, it is preferable that the ratio of the active ingredient including at least one of a protein having matrix metalloprotease 3 activity or the matrix metalloprotease 3 precursor protein, is 12 ng/ml-1000 ng/ml.

It is preferable for the above pulp stem cells in this invention to have at least one of pulp SP cells, CD31-negative and CD146-negative cells, CD24-positive cells, CD105 positive cells or CD150 positive cells.

A screening method relating to the third point of view of this invention is a screening method of the active ingredients of the medicaments for treatment of pulpitis and/or acceleration of dentin formation. It is characterized by three processes: (1) a step for measuring gene expression of matrix metalloprotease 3 in pulp stem cells or endothelial cells to which test compounds are supplied, (2) a step for measuring gene expression of matrix metalloprotease 3 in pulp stem cells or endothelial cells to which test compounds are not supplied, and (3) a step for choosing a process to choose the compound which increase gene expression of matrix metalloprotease 3 when compared in both matrix metalloprotease 3 expression, as an active ingredient of the above mentioned medicaments.

Advantages of the Invention

Since the medicaments relating to this invention reduces the inflammation state of pulpitis stimulate migration and the anti-apoptotic effect of the endothelial cells, and promotes proliferation of pulp stem cells and endothelial cells under injury site, angiogenesis/vasculogenesis and the dentin formation, it is useful for treatment of pulpitis. In addition, the dental materials relating to this invention reduces the inflammation of pulpitis by filling in the cavity on the dental pulp tissue, and further accelerate dentin formation by stimulation of proliferation of pulp stem cells and endothelial cells under injury site and angiogenesis/vasculogenesis. In addition, it is possible for the screening method relating to this invention to select precisely an active ingredient of the medicaments for pulpitis treatment and/or acceleration of dentin formation from test compound by comparing the gene expression of matrix metalloprotease 3.

DESCRIPTION OF EMBODIMENTS

Figure 1A:
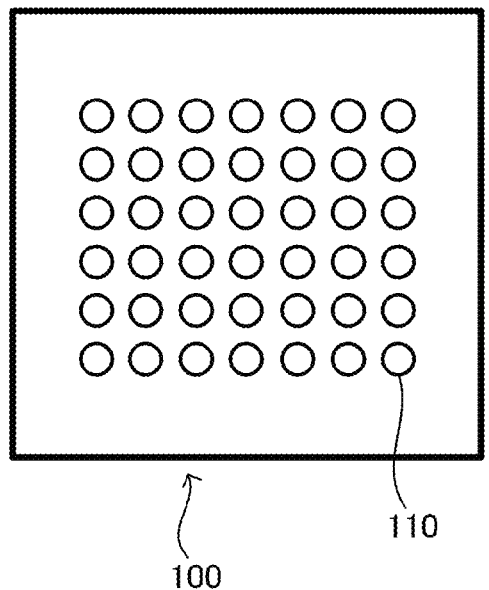
FIG. 1A is a ground plan of a membranous carrier having recesses.

Favorable embodiments of the present invention will be described specifically below with reference to the attached figures.

This invention relates to medicaments for treatment of pulpitis and/or acceleration of dentin formation containing at least one of either protein having matrix metalloprotease 3 activities or matrix metalloprotease 3 precursor protein as an active ingredient, dental materials and a screening method.

In these embodiments of the present inventions, the medicaments utilizes both pulpitis treatment and/or acceleration of dentin formation by matrix metalloprotease 3. Matrix metalloprotease 3 belongs to the matrix metalloprotease (MMP) family, and is considered to be implicated in the degradation of the extracellular matrix. However, the characteristics of each MMP are not known yet.

The present inventors discovered that MMP3 specifically has a role in acceleration of dentin formation, among many variety of proteins highly expressed in subfraction of SP cells based on the gene expression profile of subfraction of SP cells isolated from pulp cells. Since various studies have been done concerning MMPs and MMP3 has a function in degradation of various kinds of cartilage matrix, MMP3 is known to be implicated in rheumatism or use as the marker as a protein relevant to the cartilage destruction. In addition, related to destruction of periodontal ligament in periodontal disease, an expression inhibitor of the MMP3 gene is tried to be utilized as the prevention of the periodontal disease or a therapeutic agent, trying it is done (Japanese Patent Laid-Open No. 2006-298,913 bulletin). However, usage for healing of pulpitis by MMP3 has not been reported. In addition, it is not known at all that MMP3 in involved in repair and regeneration of pulp and/or dentin.

The present medicaments and dental material is to apply protein with matrix metalloprotease 3 activities to injury and/or inflammation site directly, has potential acceleration of pulp healing in pulpitis according to the medicaments and the dental materials of the present invention. In addition, it can enhance repair/regeneration of pulp and/or dentin according to the medicaments and the dental materials.

Such advantages of this invention is not limiting to this invention, but is suggested to be a special function of MMP3 that stimulates migration of endothelial cells and endothelial progenitor cells to an injury site, enhances proliferation and anti-apoptosis, and accelerates pulp regeneration and dentin formation through enhanced vascularization.

Various embodiments of the present invention will be explained below.
(Medicaments for Pulpitis Treatment and/or Acceleration of Dentin Formation)

The medicaments of this invention contains protein having MMP3 activity (MMP3 activity protein), MMP3 precursor protein or these mixtures as an active ingredient. MMP3 protein is defined as MMP3 activity protein, MMP3 precursor protein or these mixtures hereafter. MMP3 is a kind of protein belonging to the MMP family, and MMP3 is referred to stromelysin 1. MMP3 is acquired by a various biological species, and human MMP3, for example, can acquire an amino acid sequence and the base sequence in GenBank in the accession number NP_002413.1.

The MMP3 activity protein is also available in recombinant MMP3. In other words, it is acceptable to derive from *E. coli*, an insect or human fibroblasts. The MMP3 activity protein has an amino acid sequence to have either of the substitution, the deletion, the insertion and the addition of one or a plurality of amino acids of natural MMP3, or to have two more than these kinds of modification in an amino acid sequence, and should have MMP3 activity. In other words, it may be modification of MMP3 derived from natural ingredient. The acquisition of such a modification is well-known to person skilled. We can acquire it with reference to laboratory Manual, 3nd Ed., Cold Spring Harbor Laboratory, Cold Spring Harbor, N.Y., 2001 (abbreviation: molecular cloning the third edition) or Current Protocols in Molecular Biology, Supplement 1-38, John Wiley & Sons (1987-1997) (abbreviation: current protocol in molecular biology). On acquiring the modification, the MMP3 activity is measured by using gel zymography, Enzyme-linked immunosorbent assay (ELISA) or active system of measurement using fluorescent peptides (Nagase et al., J. Biol. Chem. 1994, 269:20952-20957). In addition, the degree of the MMP3 activity in the modification is not restricted in particular. MMP3 precursor protein is secreted as an inactive precursor (pro MMP3) from connective tissue cells, and a precursor before limited proteolysis of a propeptide domain, and it is the concept including the modification of the MMP3 precursor derived from nature.

The MMP3 activity protein is provided by cutting off MMP3 precursor protein artificially by trypsin, plasmin, serine protease. In other words, the MMP3 precursor protein becomes the active form after limited proteolysis of a propeptide domain by the other or own protease activity. Therefore, the deterioration of the medicaments can be prevented in the stage before applying the medicaments in vivo if MMP3 precursor protein is contained in the medicaments, and the MMP3 precursor protein is activated in vivo spontaneously or by other reactions. When a mixture of MMP3 activity protein and MMP3 precursor protein is used, the ratio of the mixture is not restricted and selected properly.

In the medicaments in the present invention, MMP3 protein can be mixed with the pharmacologically and pharmaceutically permissible additive agents, and manufactured into various preparations suitable for application to an affected part. For example, the formulations suitable for a pulp capping agent of this invention are injections, a solution for external use (injectant, liniment), solid preparation (granule, infinitesimal grain agent, powders, ointment, tablet), ointment.

For example, the pharmacologically and pharmaceutically permissible additive agents can be excipient, disintegrating agent or collapse supplement, bond, lubricant, coating agent, pigment, diluent, basis, resolvent or solubilizing agent, isotonic agent, pH modifier, stabilizer, preservative, emulsifying agent, emulsifier, gelling agent, thicking agent, adhesive agent, flavor etc. The gelling agent, for example, is acceptable to absorb the exudate of the tooth and gelate. In addition, as a form consisting of powdered medicaments and solutions, it is acceptable to mix and mingle at the time of application and may use it.

The medicaments of the present invention may contain other active ingredients such as sterilizer, antibiotic, anti-inflammatory agents.

The medicaments of the present invention is applied to the exposed pulp and the adjacent site for dental restorative and prothodontic treatment including normal caries treatment and pulp exposure and amputation after pulp injury. For example, it can be applied or filled on an access cavity, in a cavity after the pulpectomy, on dentin, on the amputated pulp. In addition, it can be applied on the regenerated pulp or in the root canal or its neighborhood after pulpectomy or root canal enlargement and irrigation of periapical disease.

The medicaments of this present invention can be used alone, or together with a direct pulp capping agent or an indirect pulp capping agent. The medicaments of this invention may be applied before or after application of a direct pulp capping agent or the indirect pulp capping agent. The medicaments of this invention may be mixed with a direct pulp capping agent or an indirect pulp capping agent. "The direct pulp capping agent" is a medicine to protect a dental pulp tissue when a part of the pulp is exposed, and, for example, calcium hydroxide preparation etc. is used. "The indirect pulp capping agent", is a medicine to protect external stimuli and sterilize when dentin in the cavity becomes thin, but dental pulp is not exposed, and, for example, zinc oxide eugenol preparation, zinc oxide creosote preparation are used.

The component ratio of the MMP3 protein in the medicaments of this invention is, for example, 12 ng/ml-1000 ng/ml, and suitable for 50 ng/ml-500 ng/ml, and am more suitable for 80 ng/ml-200 ng/ml. The reason why it is less than 10 ng/ml is that migration promotion effects on HUVEC by MMP3 may sometimes become insufficient. In addition, more than 1000 ng/ml has a possibility to cause an unexpected side effect when the medicine of this invention applies in vivo. The amount for usage of the medicine of this invention is adjusted appropriately by the symptom (progress degree of the caries, the damage/loss degree of the dental pulp) of the patient, age, a formulation without being limited in particular. The amount for usage of the medicine of this invention is for example, 1 ng-100 µg, preferably 10 ng-10 µg, and more preferably 10 ng-1 µg in dry weight per unit dosage of the MMP3 activity protein as an active ingredient.

The medicine of this invention promotes formation of pulp and/or dentin and regenerate damaged or lost tissue. Therefore, the dental pulp can be conserved effectively by applying to the exposed pulp and the neighborhood. Therefore, the medicine of this invention can be used alone as a pulp capping agent or together with another pulp capping agent.

In addition, according to the medicine of this invention, it can enhance healing or improve a symptom of pulp in pulpitis or the neighborhood of an inflammatory disease. Therefore, this medicaments of this invention can be used as a preventive agent or a therapeutic agent for pulp related disease including pulpitis or periapical disease and an inflammatory disease of the neighborhood.

(Dental Materials)

The dental materials of this invention can include a carrier having biocompatibility other than MMP3 protein. The dental materials of this invention promote pulp and/or dentin formation by the application to the part of the lost pulp and the neighborhood, leading to effective conservation and/or regeneration of pulp tissue.

(A Carrier)

In dental materials of this present invention, the carrier facilitates the application to an affected part of the MMP3 protein. In addition, the carrier holds MMP3 protein in an affected part during enough period of time to form or regenerate pulp and/or dentin. In addition, it functions as scaffold to accumulate various cells and regenerate tissue or filling materials. The carrier may be made as a complex with MMP3 protein in advance, and it may be a kit separately from MMP3 protein.

It is preferable for the MMP3 protein to be held on the surface of the carrier by some kind of interaction.

It is desirable for the carrier to have biocompatibility. For example, the materials of the carrier with biocompatibility include composition polymer materials such as PLA (polylactic acid), PGA (a polyglycolic acid), PDLLA (poly-DL-lactic acid), PLGA (a lactic acid glycolic acid copolymer), PEG (polyethylene glycol), polysilicon, PCL (polymosquito professional lactone) other than type I collagen and type III collagen, various collagen such as aterocollagen, artificial proteoglycan, glycosaminoglycan, gelatine, hydrogel, fibrin, phosphophoryn, hyaluronic acid, chitin, glucosamine, fibronectin, alginic acid, heparan sulfate, heparin, laminin, three phosphoric acid calcium, hydroxyapatitte, natural material such as µ-TCP and the derivative. In addition, for example, the materials of the carrier with biocompatibility include the inorganic materials such as calcium carbonate, titanium, gold and ceramics. In addition, the proteoglycan is a kind of the complex carbohydrate of covalent bond of protein and a carbohydrate chain (glycosaminoglycan). In addition, on the surface of the carrier of synthetic polymer materials such as polysilicons, the layer of carrier material consisting of natural material such as a plasma coat, collagen solution or fibronectin or the derivatives can be formed in consideration of cell adhesion characteristics and cell proliferative activity. In addition, plasma processing, a collagen coat may be put for the surface of the carrier to improve cell adhesive property.

Type I collagen and type III collagen are the mixed collagen which is mixture with type I collagen and the type III collagen. Type I collagen is basic collagen, and it is fibrous collagen. The type III collagen forms structure of thin network, called reticular fiber different from the collagen fiber, and make scaffold for cells etc. The ratios of the type III collagen in the mixed collagen, is preferably more than 30% and less than 50% by weight. The reason for it is when ratio of the type III collagen increases more than 50% by weight, the mixed collagen might not solidify. On the other hand, when ratio of the type I collagen increase and there become fewer ratio of the type III collagen than 30% by weight, a vascularization as described later, not occur but dentin is possibly regenerated. Most preferably, the mixed ratio of type I collagen and the type III collagen is 1:1 by the weight.

In addition, sponge-shaped three dimensional structure consisting of the nanofiber, average diameter 1 nm-1,000 nm manufactured with the macromolecules such as thermoplastic macromolecules also can be used as a carrier with biocompatibility. It is preferable for the porosity of such a three-dimensional structure body to be 80%-99.99%. In addition, a cross section or a longitudinal section of the sponge-shaped three-dimensional structure are observed by a scanning electron microscope. The cross section of 150 filaments extracted in an equivalence aspect at random are analyzed by image processing software and a diameter of the circle conversion is used to measure average diameter.

The three-dimensional form of the carrier does not be restricted in particular, but can take various forms such as form of filament, film, fiber condensed shape, mesh, sponge, the microgranulation. In addition, it coats an exposed pulp and may comprise the shape to fit for the three dimensions form of the cavity (cavity restoration form) which occurred after pulpectomy or pulpotomy.

It is preferable that the carrier holds MMP3 protein or has the surface to which cells easily attach. More preferably, the carrier is porous object or a reticular frame object which are easy to secure surface area and space. Furthermore, it is preferable that the carrier, its material in structure or its material itself has oxygen permeability or material permeability.

The carrier can use in combination with materials with different three-dimensional forms. For example, a carrier with porous object (porous structure) suitable for scaffold to cover the surface of exposed pulp and to fill in the cavity on the upper part of the exposed pulp may be combined together with a carrier suitable for scaffold for dentin regeneration in more upper part of the cavity. In this case MMP3 protein may be adsorbed in either of the carriers, but it is more effective to adsorb MMP3 protein in a carrier of the pulp side to promote regeneration.

To hold MMP3 protein in the carrier, MMP3 protein can adhere to a carrier if the dental material contains the carrier. It is acceptable just to let both come into contact by merely mixture or impregnation when the carrier is easy to adsorb MMP3 protein by interaction.

The carrier suitable for scaffold for dentin regeneration can use carrier 100 with many recesses comprising minute concavity recesses (pores) 110 in its surface as shown in FIG. 1A. Such recesses (pores) 110 can be formed in a structure similar to that of the dentinal tubules. Recesses 110 do not have to be completely mimic to the dentinal tubules, but it is desirable to be formed in size (a diameter and depth), orientation characteristics and formation interval (pitch) of the dentinal tubules. The reason is because dentin regeneration is promoted in the carrier comprising such recesses 110.

Figure 1B:
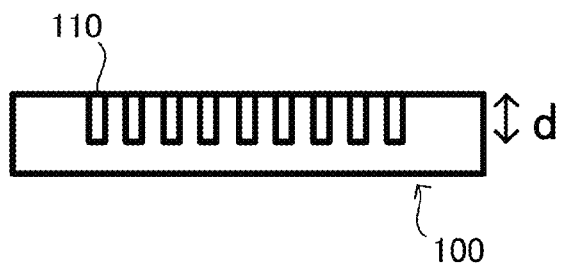
FIG. 1B is a side view of a membranous carrier having recesses.
Figure 1C:
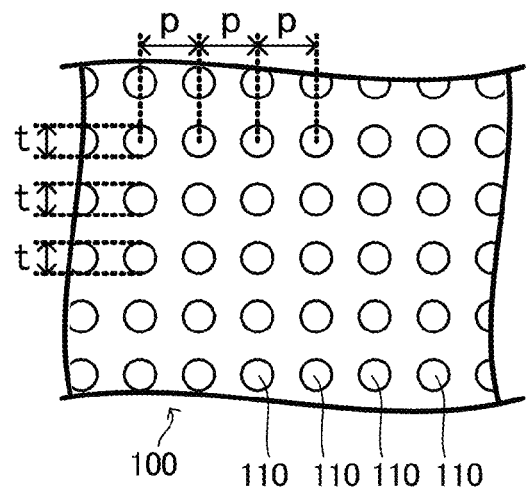
FIG. 1C is an illustration to enlarge the portion of recesses to explain.

Recesses 110 have an opening at least in the one side surface of carrier 100 with recesses as shown in FIG. 1B. Depth d of recesses 110 is formed, for example, at around 1 µm-10 µm and is preferably less than 15 µm more than 1 µm and is more preferably less than 13 µm more than 1 µm and is less than 10 µm more than 2 µm, more preferably. In addition, concave diameter t of recesses (pores) 110 and pitch p are formed in a few µm-a few 10 µm, for example, as shown in FIG. 1C. For example, concave diameter t of recesses (pores) 110 is more than 1 µm and less than 12 µm, and is preferably more than 1 µm and less than 10 µm, and is more preferably more than 2 µm and less than 8 µm. For example, concave pitch p of recesses (pores) 110 is more than 2 µm and less than 30 µm, and preferably more than 3 µm and less than 30 µm, and more preferably more than 4 µm and less than 26 µm. In such recesses 110, it is preferable to be opened many to the pulp side to cover exposed pulp. A pulp cross section is approximately 1 mm². In recesses 110, it is preferable to be formed approximately around 5,000-50,000/mm² for pulp (exposed pulpal side). In addition, recesses 110 may be formed in non-penetration that does not go through the other side of the carrier, and it may be a through-hole. Preferably recesses 110 is a non-penetration. The thickness of carrier 100 with the recesses is not restricted in particular, but, for example, 200 µm-1,000 µm.

As for carrier 100 with the recesses, the carrier is preferable to consist of materials with oxygen permeability or material permeability. The reason is because it can promote odontoblast differentiation and the dentin formation more. Such a material typically includes silicone resin. If use silicon, the concavity recesses can be formed at the same time when the three-dimensional shape is formed to fit for a cavity restoration form, namely when molding, without forming a recesses by back processing by lasers For example, a concavity recesses can be formed at the same time of molding by preparing a mold with the cavity suitable for a restoration form to comprise a molding part (a special convex department) that can form dentin tubules-like recesses. In addition, as for the support material made by silicone resin, it is easy to be eliminated after having located it in affected parts during a scheduled period. In addition, carrier 100 with the recesses can be formed, for example, of silicon hydrogel. The silicon hydrogel is composed of copolymer with a polysiloxane frame and the polycarbonate frame and hydrophilic polymer which polymerized the hydrophilic monomer, and can use transparence gel having the mutual reticular structure of this copolymer and hydrophilic polymer. It can be formed of elastomer such as polydimethyl siloxane (PDMS), dimethyl siloxane glycerol meta acrylate, hydroxyethyl meta acrylate as well as silicon hydrogel.

When cells are plated and cultured on the carrier 100 with the recesses, the usual culture medium of the animal cells with normal serum or without serum and the culture conditions (e.g., around 37° C., a 5% $CO_2$ bottom) of the normal animal cells can be used. One may culture it in a suitable nutrient medium after one prepare for carrier 100 with the recesses, and hold it in a suitable support to maintain this carrier in the state that attached the pulp derived cells to the surface with the opening of recesses 110 of the carrier. Furthermore, an opening of recesses 110 of the carrier is immersed facing the lower part to a liquid nutrient medium. The cells are cultured while repeating pressure from the surface of this liquid nutrient medium along a depth direction of concavity recesses 110 of the carrier, to attach to the carrier, stand in a row and differentiate into odontoblasts. The pressure movement can depend, for example, on mechanical pressure. The mechanical pressure is not restricted in particular, but there is a possibility that too much high pressure give damage to stem cells or odontoblasts. Thus, it is preferably, for example, more than 0.75 $N/cm^2$ less than 1.5 $N/cm^2$, more preferably more than 0.85 $N/cm^2$ less than 1.25 $N/cm^2$, further more preferably more than 0.95 $N/cm^2$ less than 1.0 $N/cm^2$. In addition, the pressurization movement is for the liquid nutrient medium filled in a container, from one time to ten times per minutes, several seconds to around ten seconds per one pressure. More preferably, it is pressured more than three times and lower than eight times. It is preferable for the degree of the pressure not to disturb proliferation of the cells. By culture after the pressure movement, odontoblasts can form dentin.

In addition, when attach epithelium cells to the reverse side of the opening side of recesses 110 of carrier 100 with the recesses, the epithelial cells could differentiate into ameloblasts with differentiation of odontoblasts by the former pressure movement.

When plating and culturing of pulp stem cells in the recesses on the opening side of carrier 100 with the recesses, one may culture on a another different carrier (MMP3 activity protein adhesion carrier) which adsorbed MMP3 activity protein to an opening side, contacting with the carrier. Another carrier becomes a scaffold for newly differentiating odontoblasts and the MMP3 activity protein adsorbed in it promotes odontoblastic differentiation.

Carrier 100 with the recesses covers a regenerated pulp after pulpectomy or an exposed pulp after pulpotomy directly. Carrier 100 with the recesses can be fitted in the cavity which is produced after pulpectomy or pulpotomy, especially, in at least one part of the three dimensional form of the cavity in the dentin. In addition, the carrier with MMP3 protein adsorption can be located in the pulpal side of the cavity which is produced after pulpectomy or pulpotomy (usually the root side), and carrier 100 with the concavity recesses may locate in one, the surface side of the cavity (usually the crown side). In addition, the carrier 100 with the recesses faces the opening of dentinal tubules-like recesses 110 to the pulpal side. The carrier 100 with the recesses and the carrier with MMP3 protein adsorption may be manufactured individually, and may be placed or transplanted after treatment procedure. In addition, it may be located after treatment followed by unifying of the carrier 100 with the carrier with MMP3 protein adsorption to become in the predetermined form.

Figure 2A:
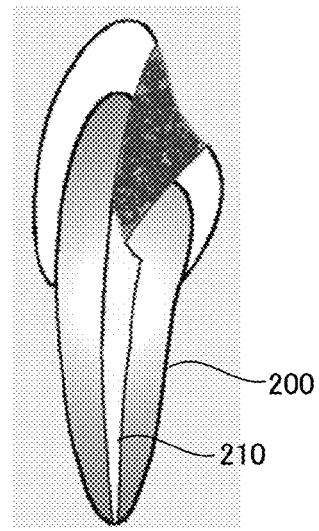
FIG. 2A is an illustration showing the tooth which dental pulp is exposed by a deep caries.
Figure 2B:
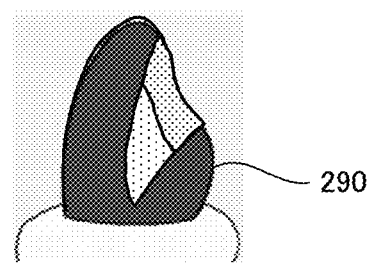
FIG. 2B is an illustration showing the model of the impression of the tooth.
Figure 2C:
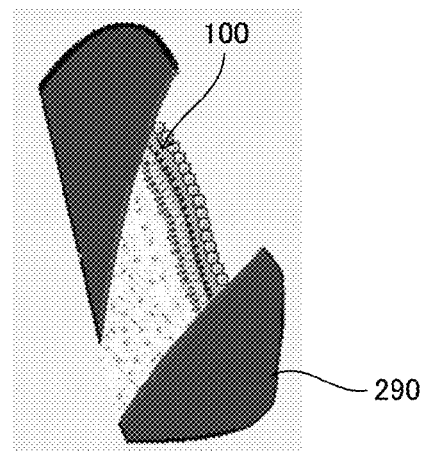
FIG. 2C is an illustration explaining the state that put the carrier with the recesses to which mesenchymal stem cells attached in the cavity of the model of the impression of the tooth.
Figure 2D:
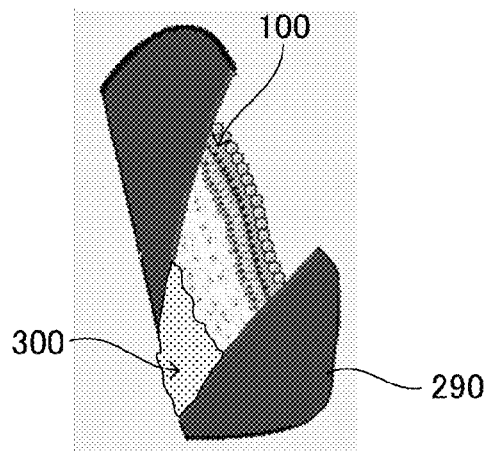
FIG. 2D is an illustration explaining the state that put the carrier in which MMP3 activity protein absorb and the carrier with the recesses in the cavity of the model of the impression of the tooth.
Figure 2E:
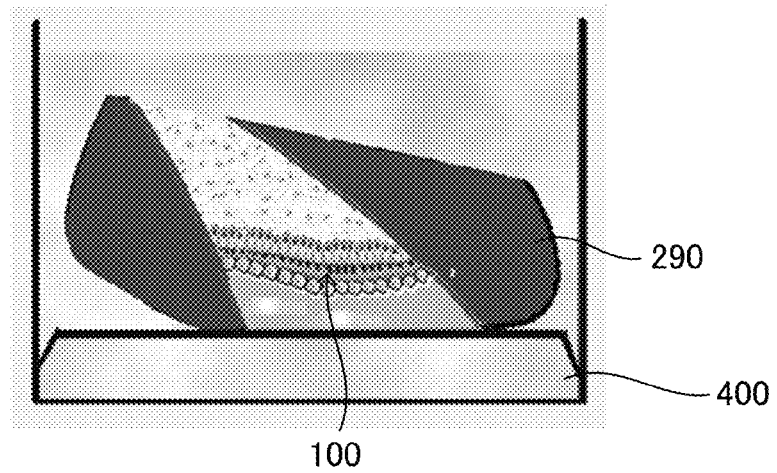
FIG. 2E is a schematic diagram explaining a state to culture stem cells in a culture device.
Figure 2F:
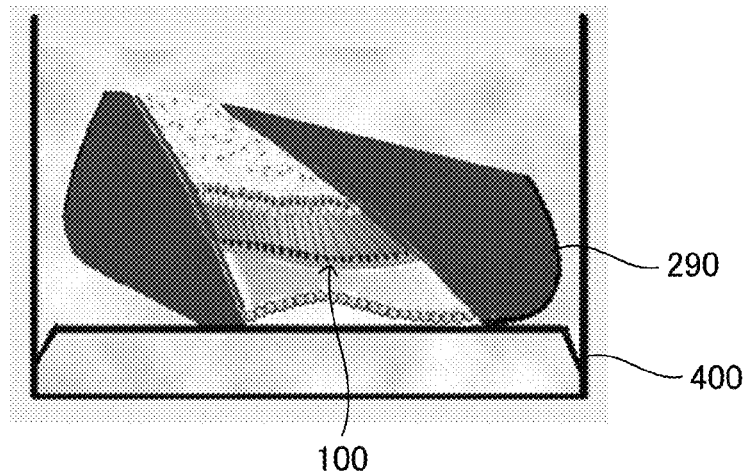
FIG. 2F is a schematic diagram explaining a state to induce odontoblast and ameloblast differentiation from stem cells for perpendicular pressure.
Figure 2G:
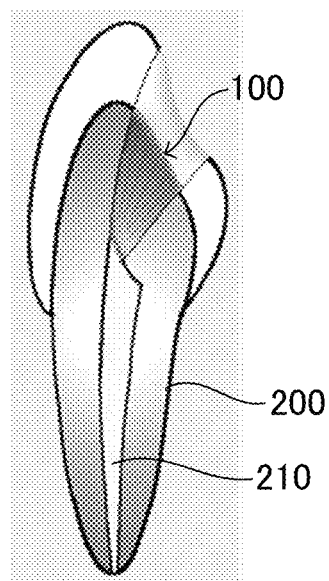
FIG. 2G is a schematic diagram explaining a state to transplant the carrier with recesses in the cavity of the tooth.

The use of carrier 100 with the recesses and the carrier with MMP3 protein adsorption will be explained using FIGS. 2A-2G. The FIGS. 2A-2G are figures showing schematically the process that tubular dentin and enamel are formed with carrier (a film) with the recesses 100. At first pulpotomy is performed when pulp 210 is exposed by a deep caries in targeted tooth 200 as shown in FIG. 2A. Then, the impression (mold) of the tooth is taken physically as shown in FIG. 2B and make model 290. In addition, it can be manufactured with a measurement by computer without taking the impression of the tooth physically. Then, mesenchymal stem cells such as pulp derived stem cells or the progenitor cells are attached to the processing surface of recesses 110 of carrier 100 with the recesses as shown in FIG. 2C and can be filled in the cavity of the mold 290 of the model of the tooth. Here, epithelium cells such as oral mucosa epitheliums can be attached to the other side of the processing surface of recesses 110 of carrier 100 with the recesses. In addition, the carrier with MMP3 protein adsorption 300 can be injected in the pulpal side of the cavity in the mold of the tooth (the root side) as shown in FIG. 2D. Furthermore, I may be injected stem/progenitor cells derived from pulp into the carrier with MMP3 protein adsorption 300. Then, three dimensional culture of mesenchymal stem cells is performed in culture device 400 as shown in FIG. 2E I after perpendicular pressure along a depth direction of recesses 110. The cells are localized in parallel in a row and differentiate into odontoblasts and ameloblasts to form dentin and enamel when cultured three dimensionally for a while as shown in FIG. 2F. Then, the cells are transplanted in the cavity facing the recesses 110 of carrier 100 with the recesses underneath, and the cavity is closed by resins as shown in FIG. 2G. At this time the carrier MMP3 protein adsorption 300 may put in an exposed pulp side or amputated pulp as described above, and carrier 100 with the concavity recesses which does not attach stem/progenitor cells derived from pulp may sometimes be put on its top directly. Pulp, tubular dentin and enamel (enamel is formed when the epithelial cells such as oral mucosa epitheliums attaches to the other side of the recesses of carrier 100 with the recesses) are formed in this way.

Carrier 100 with the recesses may cap an exposed pulp surface in itself. It is effective just to hold MMP3 protein to this carrier and transplant it if the amputated site is shallow.

(Dental Pulp Cells)

The dental materials of this invention can include carriers with cells or cells that are replacement for carriers, and more than one kind or two kinds are chosen among the cells; pulp cells, pulp stem cells, pulp progenitor cells, cells that potentially differentiate into pulp cells, odontoblasts, and cells that potentially differentiate into odontoblasts. When they include such cells, pulp and/or dentin formation/regeneration is still more accelerated after transplantation in the lost part. Especially pulp cells, pulp stem cells, pulp progenitor cells and the cells which can differentiate into pulp cells promote pulp and dentin formation and regeneration, and odontoblasts and the cells that can differentiate into odontoblasts promote dentin formation and regeneration. As for the dental materials of this invention, it is desirable that these cells can attach and be held to proliferate to the carrier as a scaffold. It is preferable that the content of such cells (pulp cells, pulp stem cells, pulp progenitor cells, cells which can differentiate into odontoblasts) is more than $1 \times 10^3$ cell/μl and less than $1 \times 10^6$ cells/μl. The reason for it is that acceleration of pulp and dentin formation and regeneration may become insufficient if fewer than $1 \times 10^3$ cells/μl. On the other hand, another reason for it is that an unexpected side effect may occur if more than $1 \times 10^6$ cells/μl is filled in the cavity in vivo.

The pulp stem cells are stem cells derived from permanent teeth or deciduous teeth. The pulp cells derived from human deciduous teeth contain $CD105^+$ cells, representing approximately 50% (while $CD31^-SP$ cells derived from human permanent teeth contain $CD105^+$ cells, approximately 20%). The pulp cells derived from human deciduous teeth show in particular angiogenic potential in vitro, and enhance recovery of blood flow and angiogenesis/vasculogenesis in the hindlimb ischemia.

The pulp stem cells are human pulp SP cells, $CD31^-/CD146^-$ cells, $CD24^+$ cells, $CD105^+$ cells or $CD150^+$ cells. For example, the human pulp SP cells have a high regenerative potential such as angiogenic/vasculogenic potential. Specifically, in the vascularization in the hindlimb ischemia, the human pulp SP cells have 1.2 times more vascularization ability in comparison with human deciduous pulp cells. In addition, the human pulp SP cells have 2.6 times more vascularization ability in comparison with human permanent pulp cells.

For example, these cells can be isolated from human extracted teeth. The human pulp cells are, for example, isolated according to the method by Nakashima M. Archs oral Biol. 36 (9), 655-663, 1991. In addition, the cells that a can differentiate into human pulp cells can be isolated, for example, by the following methods. Unerupted teeth are taken out aseptically and kept in suitable stock solutions such as the Phosphate Buffered Saline solution. (abbreviate it to PBS as follows). The calcified part in teeth is removed, and the pulp tissue is cut into pieces and washed using PBS solution. Subsequently it is preferable to treat the tissue using collagenase or dispase. After digestion with enzyme, cells are collected by pipetting and centrifuge. It is preferable to be allogenic cells, and 1 is more preferably autologous cells. Such cells may be cultured cells.

The odontoblastic isolation method is that recombinant bone morphogenetic proteins (BMPs) (more than one kind chosen among BMP2, BMP7 and BMP11 or two kinds) or their genes are applied to or transfected into pulp cells, pulp stem cells or pulp progenitor cells and two-dimensional or three-dimensional culture are performed in Dulbecco's Modified Eagle Medium (DMEM) with 10% calf serum and 50 μg/mL ascorbic acid to differentiate into odontoblasts and isolate.

For example, the cells that can differentiate into odontoblasts are pulp cells, pulp stem cells or pulp progenitor cells. The pulp cells can be isolated by enzyme digestion method (Nakashima M. Archs oral Biol. 36 (9), 655-663, 1991). Pulp progenitor cells and pulp stem cells are isolated by flow cytometry in subfraction of side population (SP) which strongly excludes Hoechst 33342. In addition, Pulp progenitor cells and pulp stem cells are isolated as CD24 positive, CD34 positive, CD105 positive, CD133 positive or CD150 positive cell using CD24, CD34, CD105, CD133 or CD150 antibody.

The dental materials of this invention can include endothelial cells or endothelial progenitor cells. The reason is because it is thought that the MMP3 activity protein promotes the migration of these cells to the injured site and stimulates proliferation of these cells to accelerate pulp and/or dentin formation together with a vascularization. It is preferable to be allogenic cells, and more preferably autologous cells. Such cells may be cultured cells.

The dental materials of this invention can include epithelial cells or their progenitor cells. The reason is because epithelial cells or their progenitor cells can differentiate into ameloblasts to form enamel, accompanied with the dentin formation/regeneration by odontoblasts. Such epithelial cells or progenitor cells can be isolated from oral mucosal epithelial cells or amnion epithelial cells. It is preferable to be allogenic cells, more preferably autologous cells. In addition, this kind of cells may be cultured cells.

The dental materials of this invention may include pulp cells, pulp stem cells, pulp progenitor cells, cells that potentially differentiate into pulp cells, odontoblasts, and cells that potentially differentiate into odontoblasts, endothelial cells, endothelial progenitor cells, epithelial cells or their progenitor cells, and for replacement of these cells or in addition to these cells, mesenchymal stem cells or undifferentiated mesenchymal cells isolated from bone marrow, the placenta and umbilical cord blood may be included.

The dental materials of this invention may be isolated after labeling of pulp cells using CD31, CD146, CD105 and VEGFR2 antibody and flowcytometric isolation of CD31 negative and/or CD146 negative and/or CD105 positive and/or VEGFR2 positive cell. Such cells were isolated by these inventors, and pulp SP cells that highly secrete and express MMP3. It is supposed that this kind of cells is enriched for pulp stem cells.

If the dental materials include the cells, they may include culture substances in which in the presence or absence of the MMP3 activity protein the cells are cultured and proliferated. In addition, if the dental materials include the cells, they may be accompanied with a carrier or may not be accompanied with a carrier. If they are accompanied with a carrier, cells (or cultured cells) might be only plated on the carrier or may have cultured after having plated on a carrier.

It is preferable that the MMP3 proteins are adsorbed to a carrier when the dental materials contain cells and carrier together. The MMP3 proteins may be given to a carrier beforehand before plating, and it may be given at the time of cell plating, after or at the time of culture.

The dental materials of this invention can include dentin matrix. It promotes dentin formation still more in injured sites to include the dentin matrix. For example, dentin matrix includes collagen, hydroxyapatitte and tricalcium phosphate. The dentin matrix can include a proteinous dentin matrix. A proteinous dentin matrix can include dentin sialophosphoprotein (Dspp), artificial proteoglycan, or dentin matrix protein (Dmp1) etc.

The dental materials of this invention can include morphogen to promote induction of differentiation into odontoblasts. For example, such morphogens include 1, 25 (dihydroxy) vitamin D3, dexamethasone, bone morphogenetic proteins (BMPs), insulin-like growth factors (IGFs), fibroblast growth factors (FGFs).

(A Screening Method)

The screening methods of this invention are consisted of three manufacture processes as follows: (1) a process to measure the expression of the MMP3 gene from pulp stem cells or endothelial cells when test compounds are supplied to pulp stem cells or endothelial cells. (2) a process to measure the expression of the MMP3 gene from pulp stem cells or endothelial cells when test compounds are not supplied to pulp stem cells or endothelial cells. (3) a process to choose the test compounds to promote the expression of the MMP3 gene in pulp stem cells or endothelial cells after comparison of the MMP3 expression in the first process with the second process. According to the screening method of this invention, the test compounds promoting the expression of the MMP3 gene in pulp stem cells or endothelial cells can be chosen. These test compounds can be used together with MMP3 protein or replacement for MMP3 protein as an active ingredient of the medicaments mentioned above.

For example, total RNA from the cells which contact with test compounds is isolated and the expression of the MMP3 gene is measured by PCR amplification production with the primers which are constructed based on base sequences of the known MMP3 protein using cDNA provided by a reverse transcription reaction. In addition, the expression of the MMP3 activity protein can be examined by measuring MMP3 activity in the culture conditioned medium of the pulp cells. The activity of MMP3 is examined by activity measurement system (Nagase J. et al., Biol. Chem. 1994 269:20952-20957) of MMP3 using gel zymography, enzyme-linked immunosorbent assay(ELISA) or fluorescent peptides etc.

Hereinafter, favorable embodiments of the present invention will be described specifically with reference to attached figures. This invention is not limited to the following embodiment.

DESCRIPTION OF EMBODIMENTS

Embodiment 1

Expression of MMP3 During the Pulpal Wound Healing Process

1. Experimental Pulp Injury Model of Rat

Figure 3A:
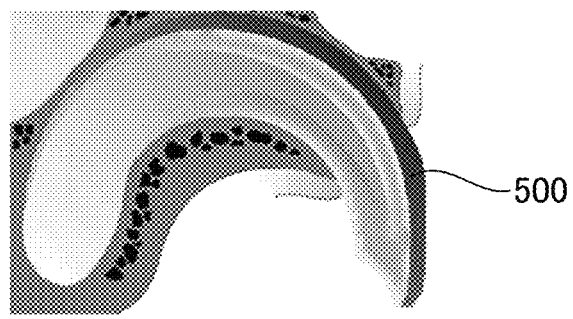
FIG. 3A is a schematic diagram explaining rat upper incisor.
Figure 3B:
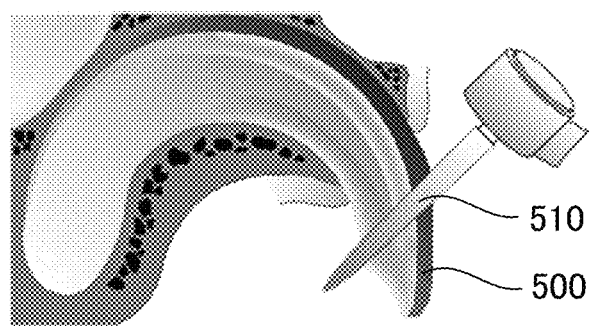
FIG. 3B is a schematic diagram explaining a state to remove the upper part of the crown of the rat upper incisor with a diamond point burr.
Figure 3C:
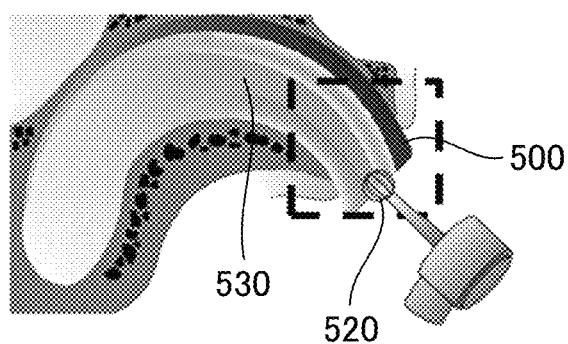
FIG. 3C is a schematic diagram explaining a state to amputate dental pulp of the rat upper incisor with a round burr.
Figure 3D:
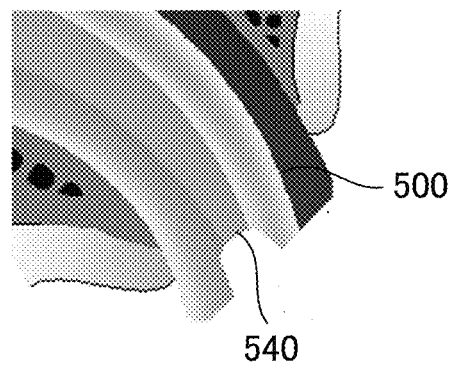
FIG. 3D is a schematic diagram explaining a state to irrigate the amputated site of the pulp and the stop the bleeding.
Figure 3E:
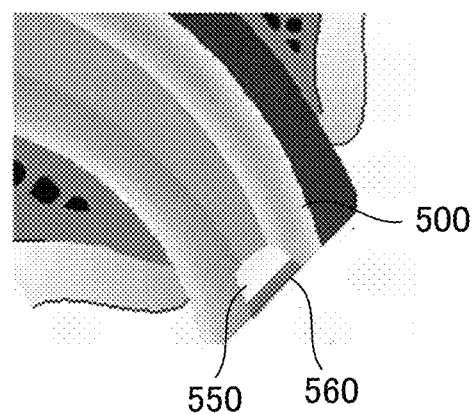
FIG. 3E is a schematic diagram explaining a state to fill with spongel and resin on the amputated site in the cavity.

Rat upper incisors 500 were prepared as shown in FIG. 3A. Eight-week male rats, weighing 220-260 g, were used (CLEA, Tokyo). As shown in FIG. 3B, the upper part of the crown, 2 mm of crown side of rat upper left and right incisors were removed with diamond point burr 510 (Shofu Tokyo, Japan). Then the pulp of the rat upper left and right incisors was amputated by No. ½ round burr 520 as shown in FIG. 3C. The amputated pulp 540 was thoroughly washed and stopped bleeding by phosphate-buffered saline (PBS) as shown in FIG. 3D. And the cavities of the amputated pulp was filled with spongel 550 and composite resin 560 (UniFil Flow, GC, Tokyo) as shown in FIG. 3E. Immediately after, 1, 12, 24, 72 hours and 7 days after treatment, rats were perfused with 4% paraformaldehyde (Nakarai tesque, Kyoto), and the incisors were extracted. The extracted upper incisors were fixed in 4% PFA at 4° C. for overnight, and decalcified with 10% formic acid for 2 weeks. The extracted upper incisors were dehydrated in ascending ethanol series and embedded in paraffin wax (Sigma) and 5 μm thick sections were cut and mounted on APS-coated slides (Matsunami, Tokyo). The slides were stored at 4° C. until used for in situ hybridization and hematoxylin and eosin (HE) histological examination. The samples for immunohistochemistry were embedded in Optimal Cutting Temperature (O.C.T.) compound (Sakura, Tokyo), 12 μm thick frozen sections were cut and mounted on APS-coated slides.

Figure 4:
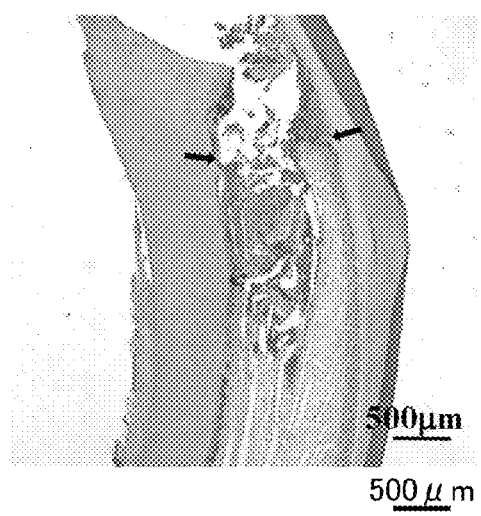
FIG. 4 is a figure of low magnification to explain a portion of pulp injury.
Figure 5A:
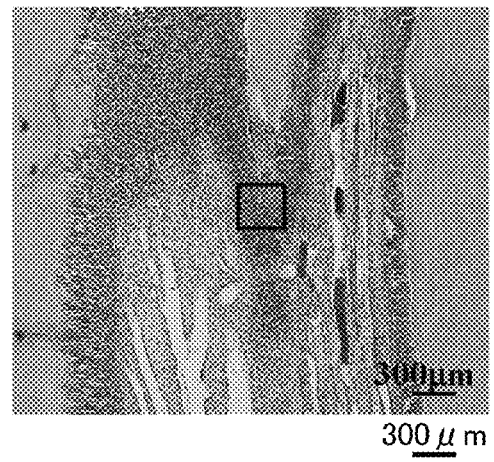
FIG. 5A is a figure of micrograph showing one hour after injury.
Figure 5B:
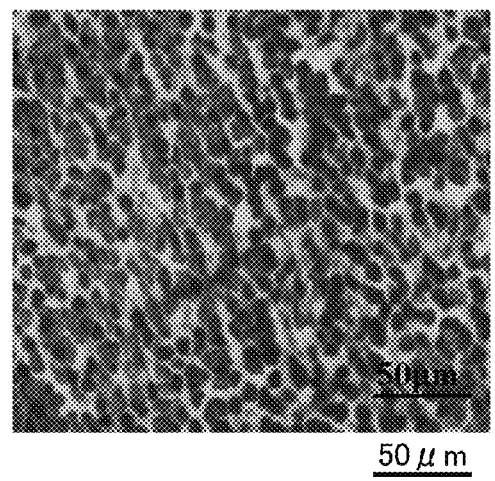
FIG. 5B is a figure of micrograph of the domain surrounded by a square in FIG. 5A.

FIG. 4 is a lower power image of the wound healing event at 12 hours after injury, and arrows indicate the amputated sites. FIG. 5A is an image of 1 hour after injury, and FIG. 5B shows a higher power image of the region enclosed in square in FIG. 5A. One hour after injury, bleeding and vasodilatation were observed as shown in FIGS. 5A and B. Immediately after injury necrosis and degeneration in rat upper part of pulp tissue were observed, and inflammatory cell infiltration mainly of neutrophils under the amputated site were seen. The whole pulp presented the edematous nature.

Figure 5C:
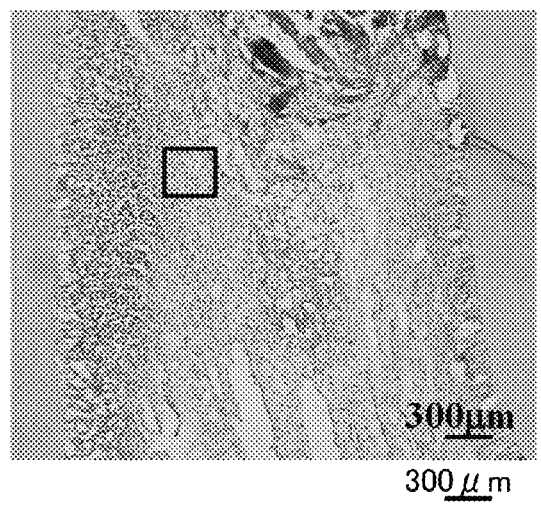
FIG. 5C is a figure of micrograph 24 hours after injury.
Figure 5D:
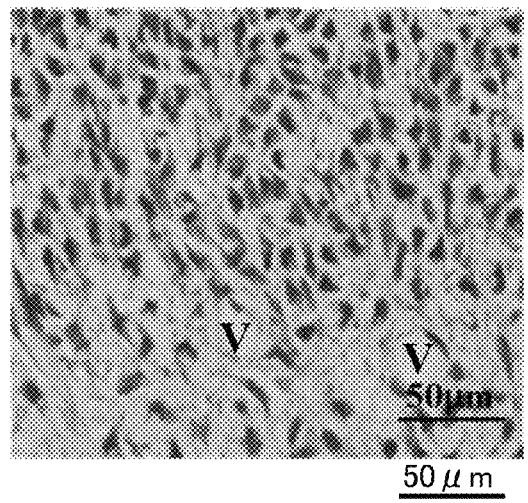
FIG. 5D is a figure of micrograph of the domain surrounded by a square in FIG. 5C.

FIG. 5C is an image of 24 hour after injury, FIG. 5D shows a higher power image of the region enclosed in square in FIG. 5C. V shows newly formed blood vessels. Much decrease of inflammatory cell infiltration were found 24 hours after injury as shown in FIGS. 5C and 5D, and a large number of fibroblastic cells, polygonal-shaped cells and newly formed blood vessels were seen underneath the degenerated pulp tissue under the amputated site.

Figure 5E:
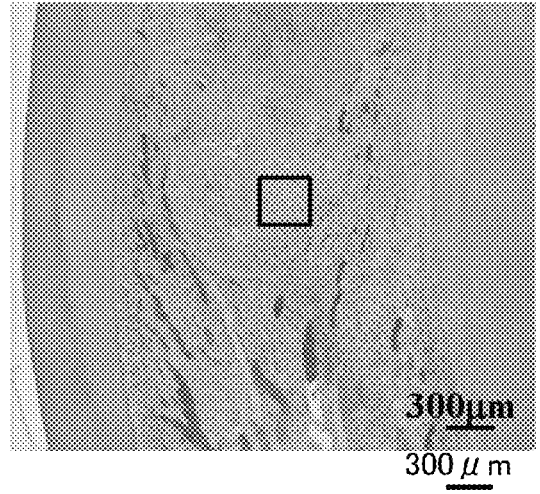
FIG. 5E is a figure of micrograph 72 hours after injury.
Figure 5F:
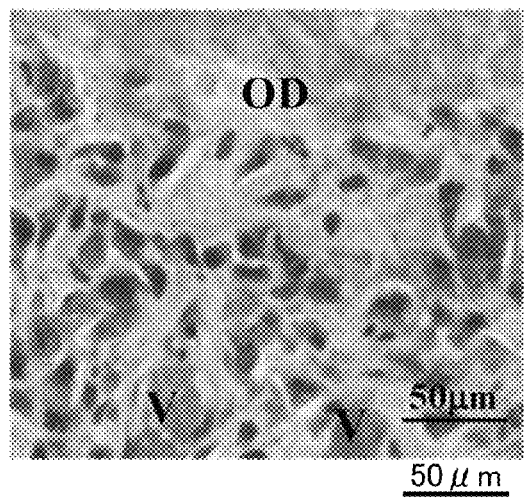
FIG. 5F is a figure of micrograph of the domain surrounded by a square in FIG. 5E.

FIG. 5E is an image of 72 hours after injury. OD shows osteodentin. FIG. 5F shows a higher power image of the region enclosed in square in FIG. 5E. Seventy-two hours later, spindle-shaped cells were surrounded by immature collagenous matrix to form osteodentin in the upper part of pulp tissue under the amputated site as shown in FIGS. 5E and 5F.

Figure 5G:
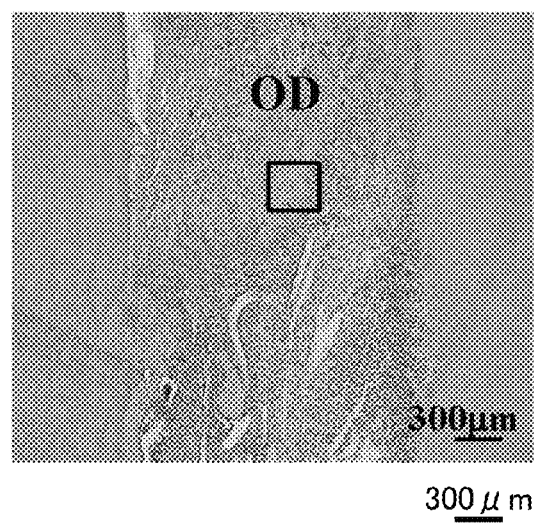
FIG. 5G is a figure of micrograph seven days after injury.
Figure 5H:
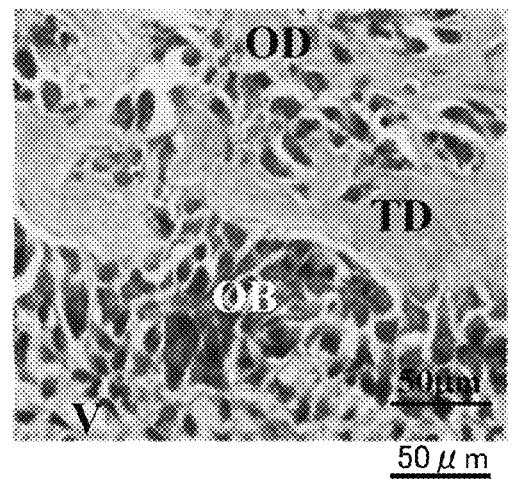
FIG. 5H is a figure of micrograph of the domain surrounded by a square in FIG. 5G.

FIG. 5G is an image of 7 days after injury. FIG. 5H shows a higher power image of the region enclosed in square in FIG. 5G. OB shows odontoblast-like cells; TD shows tubular dentin. Seven days after injury, one to two layers of well-arranged odontoblast-like cells were found to form tubular dentin under the osteodentin (OD) as shown in FIGS. 5G and 5H. The blood vessels were newly formed (V:vessel) nearly underneath of odontoblastic layers, and pulp injury was completely healed as shown in FIG. 5G. Thus, these results suggested that this pulp injury model was useful for analyzing expression and function of MMP3 during pulp wound healing process.

2. mRNA Expression During Wound Healing Process

Dental pulp tissues were isolated 0 (immediately after injury), 12, 24, 48, 72 hours after injury. The normal pulp tissue from upper incisors was used as a control. Total RNA was isolated by Trizol (Invitrogen) from the freshly extracted pulp tissues, and 2 μg RNA was reverse transcribed with ReverTra Ace-α (Toyobo, Tokyo,) following the manufacturer's recommendations. The resulting cDNA was then amplified by real-time RT-PCR with Light Cycler-FastStart DNA master SYBR Green I (Roche Diagnostics, Mannheim, Germany). Real time RT-PCR amplifications were performed at 95° C. for 10 sec, 62° C. for 15 sec, 72° C. for 8 sec. using the primers for beta-actin, MMP-1, MMP-2, MMP-3, MMP-9, MMP-10, MMP-14, VEGF, CXCR4 and SDF1 (Table 1) labeled with Light Cycler-Fast Start DNA master SYBR Green I (Roche Diagnostics, Pleasanton, Calif.) in Light Cycler (Roche Diagnostics). The design of the oligonucleotide primers was based on published rat sequences in GenBank. Melting curve analyses was performed and amplicon size of PCR products were confirmed by electrophoresis. Each RT-PCR product was subcloned into pGEM-T Easy vector (Promega, Madison, Wis., USA) and confirmed by sequencing based on published cDNA sequences. Each expression was expressed in comparison with rat normal pulp tissue after normalizing with beta-actin. The result was indicated in FIGS. 6A and 6B.

TABLE 1

| gene | | 5'-Sequence-3' | SEQ ID No | size (bp) | GenBank number |
|---|---|---|---|---|---|
| beta-actin | Forward | AAGTACCCCATTGAACACGG | No. 1 | 257 | NM_031144 |
| | Reverse | ATCACAATGCCAGTGGTACG | No. 2 | | |
| MMP1 | Forward | TTGATGGACCTGGAGGAAAC | No. 3 | 192 | EU597482 |
| | Reverse | GGTACATCAAAGCCCCAATG | No. 4 | | |
| MMP2 | Forward | GATGGCAAGGTGTGGTGTG | No. 5 | 191 | NM_031054 |
| | Reverse | AATCGGAAGTTCTTGGTGTAGG | No. 6 | | |
| MMP3 | Forward | TGGCAGTGAAGAAGATGCTG | No. 7 | 167 | NM_133523 |
| | Reverse | GCTTCCCTGTCATCTTCAGC | No. 8 | | |
| MMP9 | Forward | CGCTTGGATAACGAGTTCTCTC | No. 9 | 163 | NM_031055 |
| | Reverse | GCAGGAGGTCATAGGTCACG | No. 10 | | |
| MMP10 | Forward | ACCCCACTCACATTCTCCAG | No. 11 | 163 | NM_133514 |
| | Reverse | CATCGAAGTGAGCATCTCCA | No. 12 | | |
| MMP14 | Forward | AGTCAGGGTCACCCACAAAG | No. 13 | 204 | NM_031056 |
| | Reverse | GGTATCCGTCCATCACTTGG | No. 14 | | |
| VEGF | Forward | CTACCTCCACCATGCCAAGT | No. 15 | 183 | NM_031836 |
| | Reverse | ACACAGGACGGCTTGAAGAT | No. 16 | | |
| CXCR4 | Forward | TCCGTGGCTGACCTCCTCTT | No. 17 | 210 | NM_022205 |
| | Reverse | CAGCTTCCTCGGCCTCTGGC | No. 18 | | |
| SDF1 | Forward | GCTCTGCATCAGTGACGGTA | No. 19 | 184 | NM_022177 |
| | Reverse | TAATTTCGGGTCAATGCACA | No. 20 | | |
| Dspp | Forward | GGAACCGCAGCACAGAATGA | No. 21 | 199 | NM_012790 |
| | Reverse | CACTGTTCCCCTGTGCGTTT | No. 22 | | |
| Enamelysin | Forward | GGCGAGATGGTGGCAAGA | No. 23 | 163 | NM_001106800 |
| | Reverse | GGAAGAGGCGGTAGTTAG | No. 24 | | |

Figure 6A:
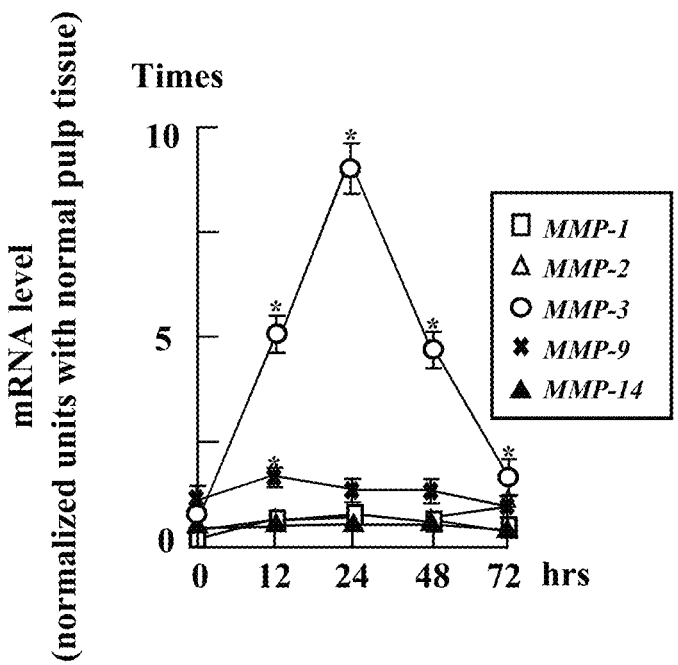
FIG. 6A is a figure showing mRNA expression changes during pulp wound healing process under the amputated site of the dental pulp. Real-time RT-PCR analysis of mRNA expression of MMP1, MMP2, MMP3, MMP9 and MMP14.

Expression of MMP-1, MMP-2, MMP-3, MMP-9, MMP-14, VEGF, SDF1 and CXCR4 mRNA was analyzed with real-time RT-PCR at 0, 12, 24, 48 and 72 hours after injury. As shown in FIG. 6A, MMP3 mRNA expression was increased till 24 hours after cutting, and became 9-fold at 24 hours compared with control normal pulp tissue. MMP3 mRNA expression then decreased to 4-fold at 48 hours and 2-fold at 72 hours compared with control normal pulp tissue. MMP-9 expression showed 2-fold at 12 hours compared with normal pulp. Its expression is low, but still maintained during pulp wound healing process. Expression of MMP-1, MMP-2, MMP-14/MT1-MMP was continuously the same level as a control normal pulp and no change during the pulp wound healing process. MMP10 mRNA expression was not observed in the normal and the wound pulp. Thus, these results suggested that MMP3 is closely related to pulp wound healing process.

Figure 6B:
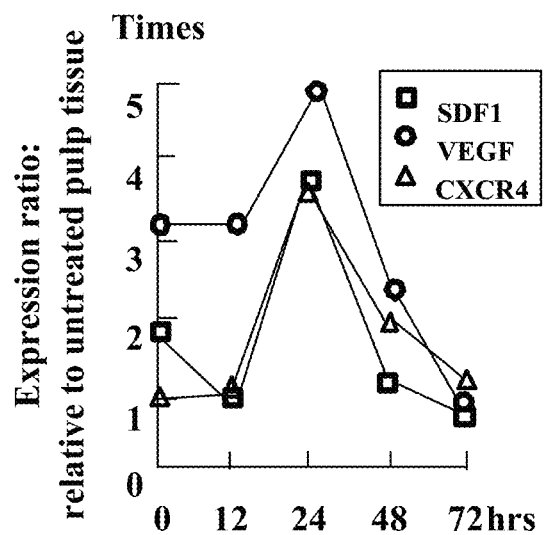
FIG. 6B is a figure showing changes of mRNA expression during pulp wound healing process under the amputated site of the dental pulp. Real-time RT-PCR analysis of mRNA expression of VEGF, SDF1 and CXCR4.

On the other hand, as shown in FIG. 6B, VEGF showed 3.5-fold expression at 0 hour after injury, then increased 5-fold at 24 hour after injury, and decreased to basal expression level at 72 hours. The expression of SDF1 reached its peak 24 hours after injury, 3.5 times compared with the normal pulp, which was relatively low. SDF1 ligand receptor CXCR4, was 3.5-fold increase in expression 24 hours after injury compared with the normal pulp.

3. Localization of MMP3, SDF1 and CXCR4 During Pulp Healing Process 24 hours and 72 hours after treatment of dental pulp, perfusion fixation was performed with 4% paraformaldehyde, followed by immersed fixation overnight. For double-staining immunohistochemistry of CXCR4 and MMP3, cryotome sections (12 μm thick) of 24 and 72 hours after injury were used. According to the normal procedure, the samples were embedded in OCT compound (Sakura, Tokyo), and 12 μm frozen sections were prepared, and mounted on APS coated slides (Matsunami Glass Ind., Osaka). CXCR4 and MMP3, and MMP3 and BS1-lectin, two types of double immunofluorescent staining were performed.

The sections were treated with 2% hydrogen peroxide for 20 minutes to block the endogenous peroxidase activity. The sections were incubated with 10 mg/mL blocking reagent (Invitrogen Corporation, Carlsbad, Calif., USA) for 1 hour at room temperature to avoid nonspecific staining, and then reacted with goat anti-CXCR4 (Santa cruze, Santa Cruz, Calif., USA) (1:50) for 1 hour at room temperature. After three washes in PBT (PBS, 0.05% Tween 20, pH 7.4), the sections were incubated with rabbit anti-goat IgG Alexa 488 (1:200) in PBT for 1 hour at room temperature. After three washes with PBT, sections were further incubated with mouse anti-MMP3 (0.5 μg/mL) in Canget 1 buffer overnight at 4° C. After three washes in PBT, bound antibodies were reacted with a HRP-labeled goat anti-mouse IgG secondary antibody (Invitrogen) for 1 hour at room temperature. Color was developed using TSA system Rhodamine-conjugated tyramide (Invitrogen). Nuclear staining was performed with Hoechst 33342 (Sigma, St. Louis, Mo., USA) at 10 ng/ml for 10 minutes, mounted with Prolong Gold antifade reagent (Invitrogen). Results are shown in FIGS. 7D-7I.

To confirm the localization of MMP3 in blood vessels, frozen sections were treated with 20 μg/ml Proteinase K (Invitrogen) for 6 minutes at room temperature. After three washes in PBS, sections were stained with 20 μg/mL of Fluorescein *Griffonia* (Bandeiraea) *Simplicifolia* lectin (BS1-lectin) (Vector laboratories, Burlingame, Calif.) for 15 minutes. This BS1-lectin has been used for specific staining of endothelial cells and endothelial progenitor cells. After three washes in PBS, sections were stained with MMP3 as described above. As negative controls, both only primary antibodies and only secondary antibodies were used. Results are shown in FIGS. 7A-7C.

Immediately after pulpotomy, neither MMP3 nor CXCR4 was expressed. FIG. 7J is the image of pulp injury surface 24 hours after pulpotomy by HE staining. FIG. 7K is showing newly formed microvessels and newly formed large vessels under the amputated pulp 24 hours after pulpotomy by HE staining. FIG. 7L is showing newly formed microvessels and newly formed large vessels 72 hours after pulpotomy by HE staining. MV shows microvessel, and LV shows larger vessel.

Figure 7A:
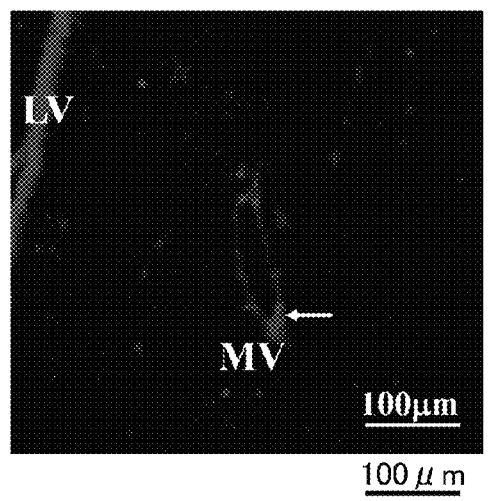
FIG. 7A is a figure of micrograph showing MMP3 expression in the immunofluorescent double staining of MMP3 and BS1-lectin 24 hours after pulp amputation.
Figure 7B:
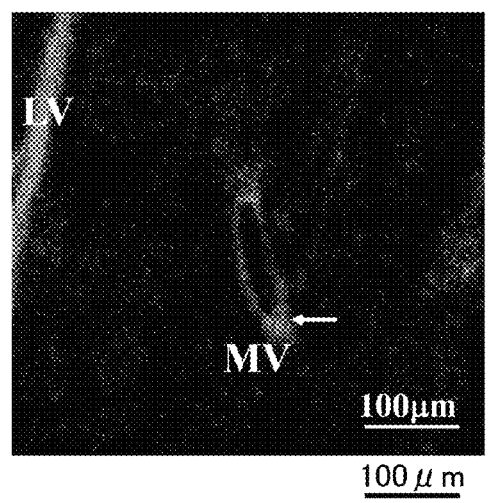
FIG. 7B is a figure of micrograph showing BS1-lectin expression in the immunofluorescent double staining of MMP3 and BS1-lectin 24 hours after pulp amputation.
Figure 7C:
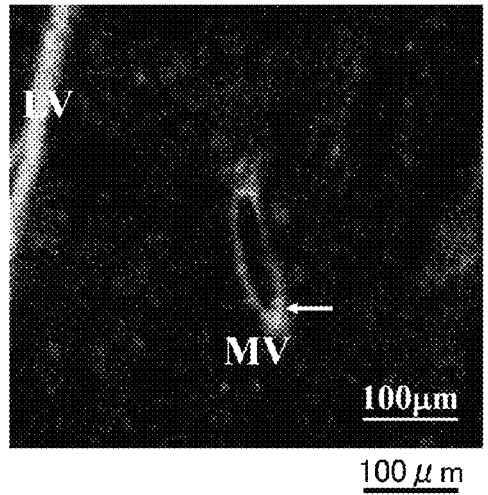
FIG. 7C is a figure of micrograph showing merged expression of MMP3 and BS1-lectin in the immunofluorescent double staining of MMP3 and BS1-lectin 24 hours after pulp amputation.

FIG. 7A shows MMP3 staining in double immunofluorescent staining of MMP3 and BS1-lectin 24 hours after pulpotomy. FIG. 7B, shows BS1-lectin staining in double immunofluorescent staining of MMP3 and BS1-lectin 24 hours after pulpotomy. FIG. 7C shows merged image in double immunofluorescent staining of MMP3 and BS1-lectin 24 hours after pulpotomy. As shown in FIGS. 7A-7C, under the surface of injured pulp MMP3 expression was detected in vicinity of endothelial cells and endothelial progenitor cell stained by BS1-lectin in the newly formed microvessels and the newly formed large vessels 24 hours after pulpotomy.

Figure 7D:
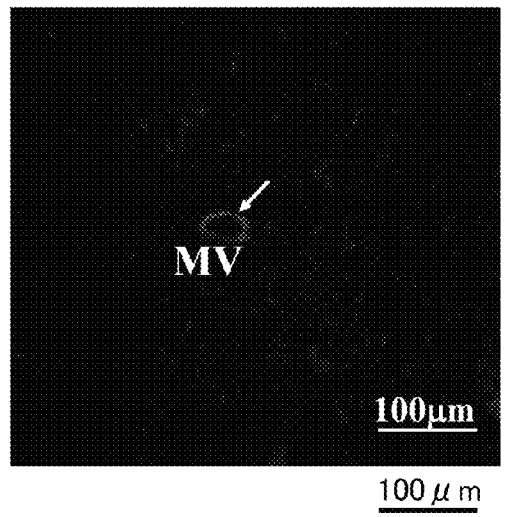
FIG. 7D is a figure of micrograph showing MMP3 expression in the immunofluorescent double staining of MMP3 and CXCR4 24 hours after pulp amputation.
Figure 7E:
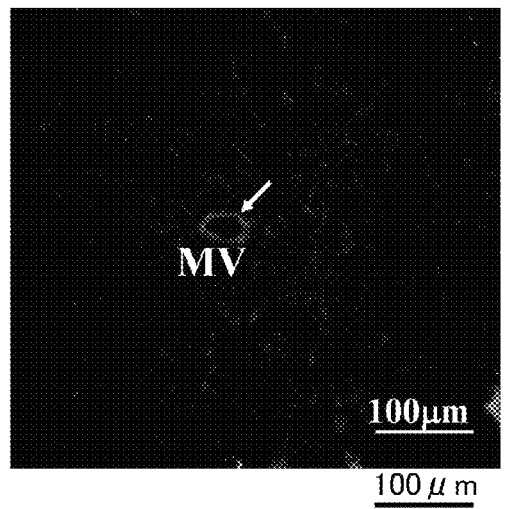
FIG. 7E is a figure of micrograph showing CXCR4 expression in the immunofluorescent double staining of MMP3 and CXCR4 24 hours after pulp amputation.
Figure 7F:
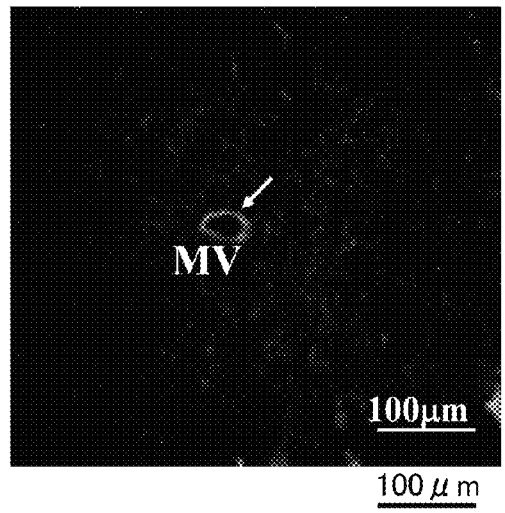
FIG. 7F is a figure of micrograph showing merged expression of MMP3 and CXCR4 in the immunofluorescent double staining of MMP3 and CXCR4 24 hours after pulp amputation.
Figure 7G:
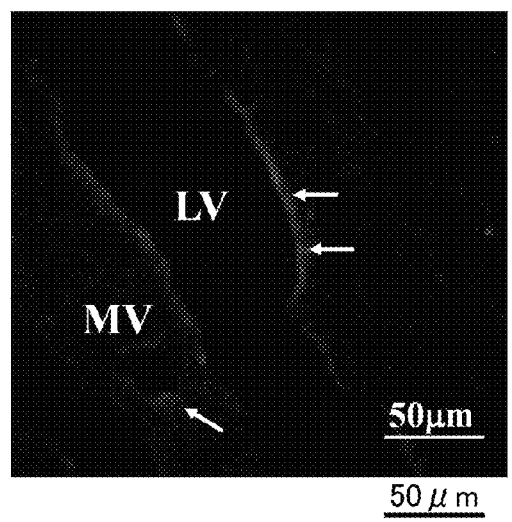
FIG. 7G is an enlarged figure of micrograph showing MMP3 expression in the immunofluorescent double staining of MMP3 and CXCR4.
Figure 7H:
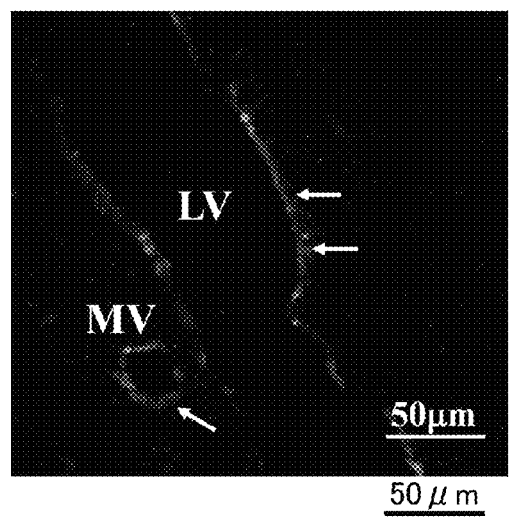
FIG. 7H is an enlarged figure of micrograph showing CXCR4 expression in the immunofluorescent double staining of MMP3 and CXCR4.
Figure 7I:
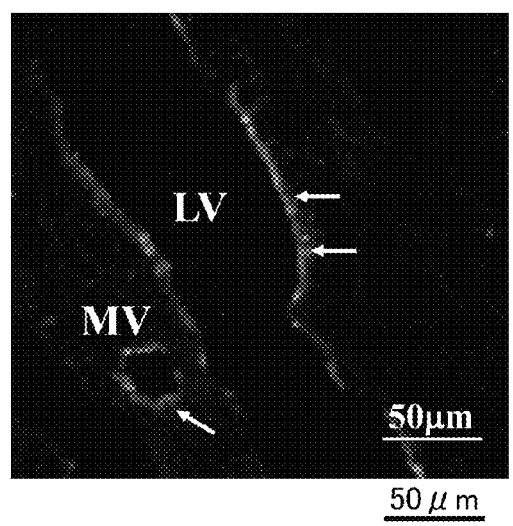
FIG. 7I is an enlarged figure of micrograph showing merged expression of MMP3 and CXCR4 in the immunofluorescent double staining of MMP3 and CXCR4.
Figure 7J:
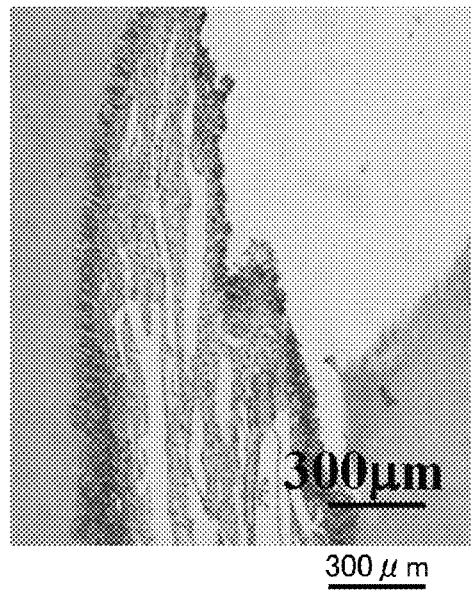
FIG. 7J is a figure of micrograph showing a pulp injury site 24 hours after pulpotomy. HE staining.
Figure 7K:
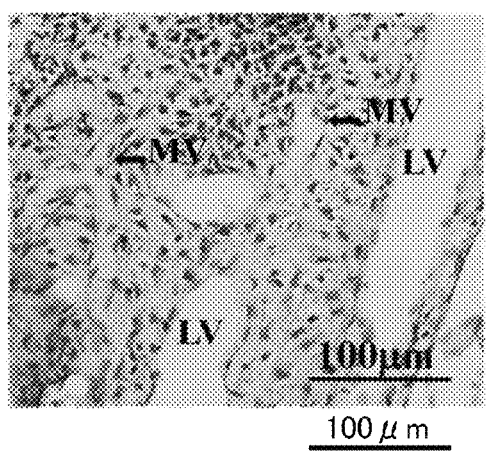
FIG. 7K is a figure of micrograph showing capillaries and regenerated larger vessels under the amputated site 24 hours after pulpotomy. HE staining.
Figure 7L:
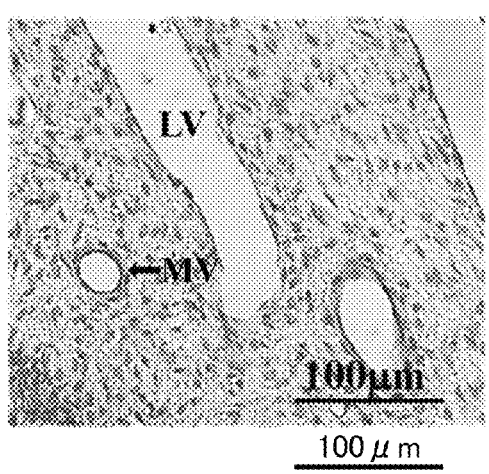
FIG. 7L is a figure of micrograph showing capillaries and regenerated larger vessels under the amputated site 72 hours after pulpotomy. HE staining.

FIG. 7D shows MMP3 staining in double immunofluorescent staining of MMP3 and CXCR4 24 hours after pulpotomy. FIG. 7E, shows CXCR4 staining in double immunofluorescent staining of MMP3 and CXCR4 24 hours after pulpotomy. FIG. 7F shows merged image in double immunofluorescent staining of MMP3 and CXCR4 24 hours after pulpotomy. FIG. 7G shows enlarged view of MMP3 in double immunofluorescent staining of MMP3 and CXCR4. FIG. 7H shows enlarged view of CXCR4 in double immunofluorescent staining of MMP3 and CXCR4. The FIG. 7I shows merged view in double immunofluorescent staining of MMP3 and CXCR4. CXCR4 is known to be a receptor for SDF1 ligand and to be expressed in stem cells. As shown in FIGS. 7D-7I, CXCR4 expression was found close to SDF1 expression. CXCR4 expression was overlapped with MMP3 expression in perivascular region.

Figure 7M:
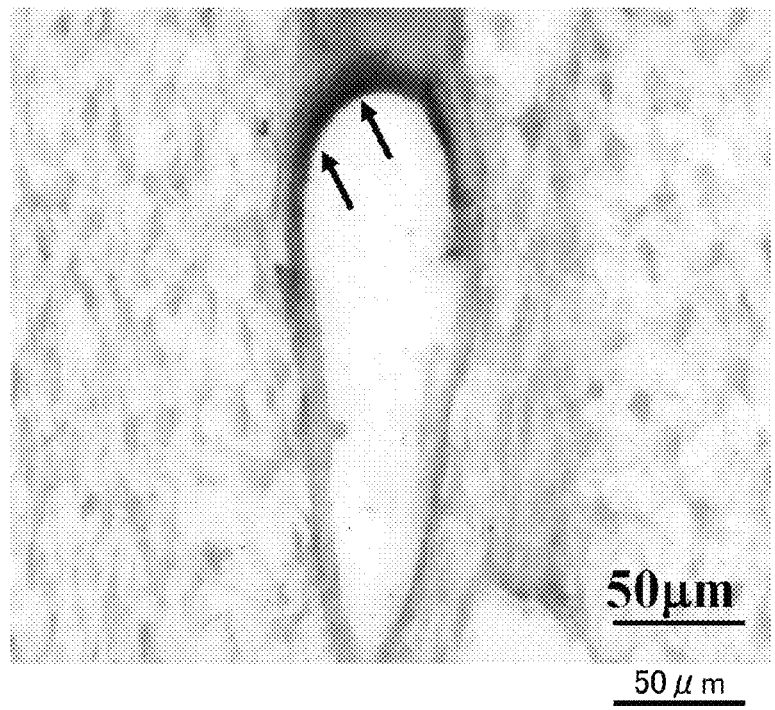
FIG. 7M is a figure of micrograph showing MMP3 mRNA expression in endothelial cells and endothelial progenitor cells 24 hours after pulpotomy by in situ hybridization.
Figure 7N:
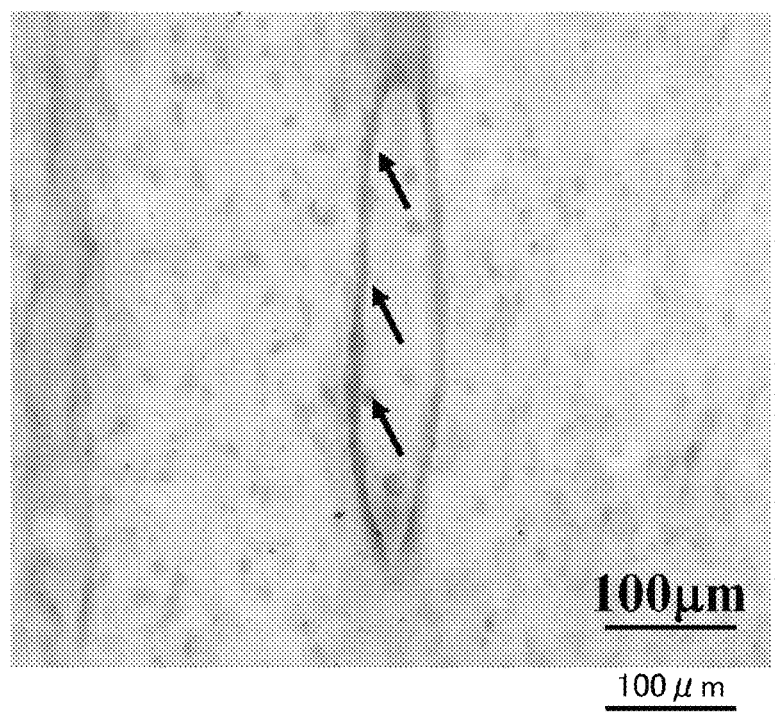
FIG. 7N is a figure of micrograph showing MMP3 mRNA expression in endothelial cells and endothelial progenitor cells 72 hours after pulpotomy by in situ hybridization.

FIG. 7M shows expression of MMP3 mRNA in endothelial cells and endothelial progenitor cells by in situ hybridization 24 hours after pulpotomy. FIG. 7N shows expression of MMP3 mRNA in endothelial cells and endothelial progenitor cells by in situ hybridization 72 hours after pulpotomy. Arrows in FIG. 7M indicate that MMP3 mRNA is expressed strongly in perivascular region 24 hours after pulpotomy. However, as shown in FIG. 7N, arrows indicate that 72 hours after pulpotomy MMP3 mRNA expression was weak. In conclusion, it is suggested that pulp stem cells migrate to perivascular region during pulp wound, secrete MMP3 to affect on vascular endothelial cells in a paracrine manner and promote angiogenesis/vasculogenesis.

Embodiment 2

Function of MMP3 in Endothelial Cells and Pulp Cells In Vitro

1. Proliferative Effect of MMP3 on Endothelial Cells

Human umbilical vein endothelial cells (HUVECs) (KURABO Industries, Osaka,) were seeded with 1,000 cells per 96 well. They were cultured in EBM2 in the presence of human MMP3 (50 ng/mL, Chemicon, Temecula, Calif.) with or without N-Isobutyl-N-(4-methoxyphenylsulfonyl)-glycylhydroxamic acid (NNGH) (0.13 μM, Biomol, Plymouth Meeting, Pa.), NNGH only, MMP-10 (50 ng/mL, R&D Systems, Minneapolis, Minn.), or VEGF-A (50 ng/mL, Peprotech, London, UK). Ten µl of Tetra-color one (Seikagaku Kogyo, Co., Tokyo, Japan) was added to the 96 well plate, and cell numbers were measured using spectrophotometer at 450 nm absorbance at 2, 12, 24, 36, 48, 60 hours of culture. Wells without cells were served as negative controls.

Figure 8A:
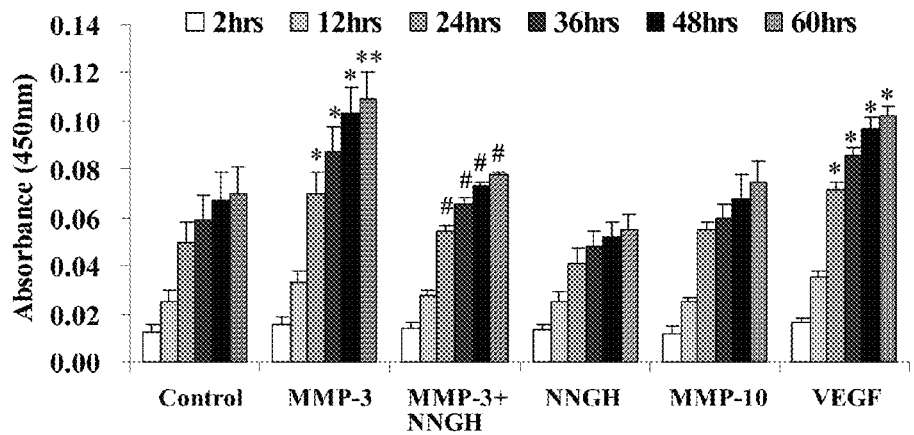
FIG. 8A is a figure showing enhanced proliferation in vitro by MMP3 in endothelial cells.
Figure 8B:
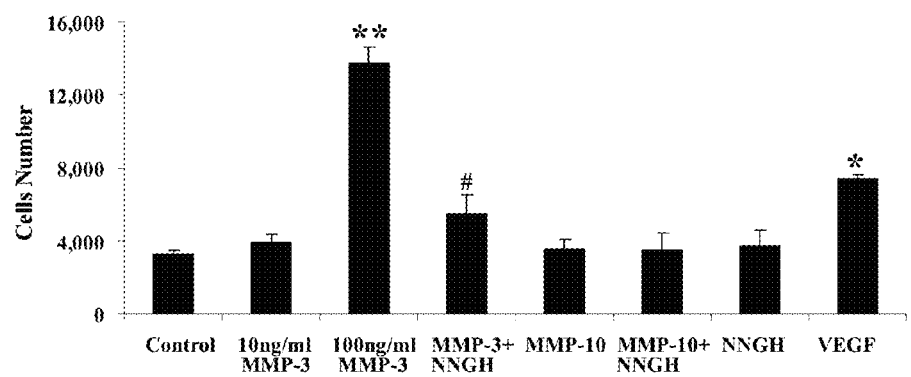
FIG. 8B is a figure showing migration effect in vitro by MMP3 in endothelial cells.
Figure 8C:
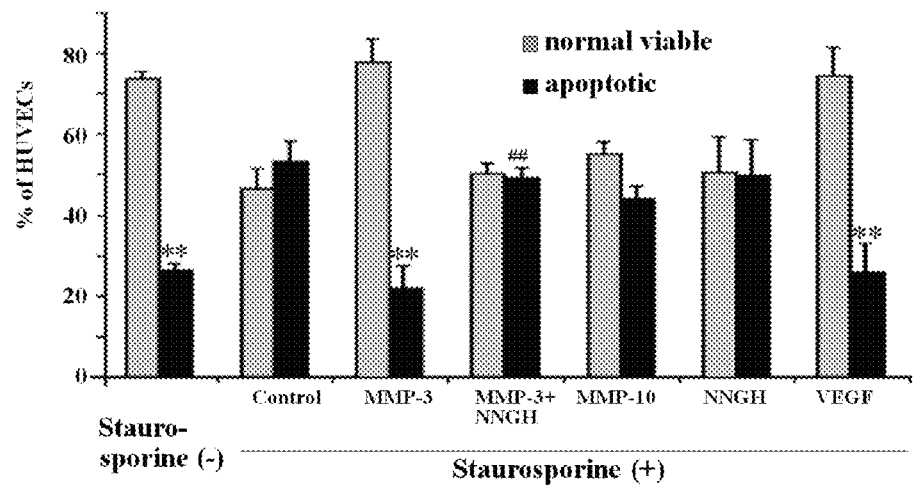
FIG. 8C is a figure showing anti-apoptotic effect in vitro by MMP3 in endothelial cells.

FIG. 8A is a figure showing proliferative effect of MMP3 in vitro on endothelial cells. FIG. 8B is a figure showing a migration effect of MMP3 in vitro on endothelial cells. FIG. 8C is a figure showing anti-apoptotic effect of MMP3 in vitro on endothelial cells. The proliferation of the endothelial cells (HUVEC) was stimulated gradually supplemented with MMP3 as shown in FIG. 8A. In MMP3 supplemented group, increase of proliferation was seen approximately 10 times more in the 48-hour application in comparison with a 2-hour application. In no addition group of MMP3, increase of proliferation was approximately 5 times more in the 48-hour effect compared with the 2-hour effect after pulpotomy. Therefore statistical significant difference was seen ($p<0.01$). On the other hand, the effect was restrained in both elapsed times when added specific inhibitor NNGH of MMP3 at the same time. The proliferative effect when added NNGH was almost the same in comparison with that of the no addition group of MMP3. In addition, the proliferative effect of MMP3 on HUVEC was approximately similar when added VEGF-A (50 ng/ml).

2. A Migration Effect of MMP3 on Endothelial Cells

Modified Boyden chamber assay was performed at 37° C. with a PET membrane (BD Bioscience, Franklin Lakes, N.J.) of 24 well for 24 hours. In the presence of 10 ng/ml of MMP3, 100 ng/ml of MMP3, 100 ng/ml of MMP3 and 0.13 µmol of NNGH, 50 ng/ml of MMP10, 50 ng/ml of MMP10 and 0.13 µmol of NNGH, 0.13 µmol of NNGH only, or 50 ng/ml of VEGF-A, $5\times10^4$ cells of HUVEC was cultured in the upper part of the chamber. As a control, a 0.02% bovine serum albumin (Sigma) was used. After incubations, HUVEC which migrated to the lower part of the membrane was detached by trypsin treatment and counted. The cells which did not migrate and remain in the upper part of the membrane were scraped by rubber scraper. The data represented the mean±SD of 4 samples. The result was shown in FIG. 8B.

As for the migration promotion effect of MMP3 on HUVEC, the significant difference was not detected in comparison with control in 10 ng/ml as shown in FIG. 8B. A significant increase, approximately 3.5 times, compared with the control was detected in 100 ng/ml ($p<0.01$). In addition, significant increase, approximately 2 times was seen in 100 ng/ml of VEGF ($p<0.01$). In other words MMP3 enhances migration in a concentration-dependent manner. The migration effect was inhibited in fact when added NNGH at the same time.

3. Anti-Apoptotic Effect of MMP3 on Endothelial Cells

To examine an anti-apoptotic effect of MMP3, HUVEC was cultured in EGM-2 in 35 mm dish for three days, and staurosporine (Sigma) was added to induce apoptosis at 100 nM in EBM-2 supplemented with 50 ng/ml of MMP3, or 50 ng/ml of MMP3 together with 0.13 µmol NNGH, or 50 ng/ml of MMP10, or only 0.13 µmol of NNGH, or 50 ng/ml of VEGF-A. NNGH was added 30 minutes before adding MMP3. As a control, cells were cultured in EBM-2 without adding any in the presence of staurosporine. Four hours later, HUVEC was detached from the dish and stained with Annexin V-FITC (Roche) and Propidium Iodide (Sigma) in a cell suspension for 15 minutes and measured ratio of necrosis and apoptosis in flow cytometer JSAN (Bay Bioscience, Kobe). The experiment was repeated three times, a representative data was shown in FIG. 8C.

As shown in FIG. 8C, apoptosis was seen in 52% of cells when added Staurosporine at 100 nM in HUVEC for four hours to induce apoptosis. The apoptotic cells was decreased to 20% when added MMP3 at the same time of Staurosporine, and an anti-apoptotic effect was similar in the case when added VEGF-A. The anti-apoptotic effect was inhibited when added NNGH at the same time. MMP10/Stromelysin-2 is an isomer of MMP3. As shown in FIG. 8A-8C, MMP10/Stromelysin-2 did not have proliferative effect, migration effect and anti-apoptotic effect which were detected in MMP3.

4. Induction of Odontoblast Differentiation by MMP3 Using Pulp Cells

Pulp cells were isolated from rat upper incisor by the trypsin and collagenase digestion method and cultured in DMEM (Sigma, St. Louis, Mo., USA) including L-ascorbic acid phosphoric acid magnesium salt (Wako pure medicine) and 10% of 50 µg/mL (v/v) fetal bovine serum (SAFC Biosciences, Lenexa, Kans., USA) and 100 unit/ml penicillin G, 100 µg/ml streptomycin (Invitrogen, Carlsbad, Calif., USA). MMP3 was added 100 ng/ml of MMP3, or 0.13 µmol of NNGH and 50 ng/ml human recombinant BMP2 to the cells at second passage of culture after confluence. Total RNA was extracted 14 days or 21 days after and analyzed expression of odontoblastic differentiation markers, dentin sialophosphoprotein (Dspp) and enamelysin by Real-time RT-PCR (table 1). Those expressions were demonstrated as relative expression to those in the rat incisor pulp cells of the second passage at confluent time after standardization with a value of µ-actin. When MMP3 was added, the differentiation inductive effect into odontoblasts in particular was not seen in comparison without adding MMP3 of the control 14 days and 21 days after treatment.

Therefore, MMP3 has stimulating effects on migration to an injured site proliferation, and anti-apoptotic effect of endothelial cells, endothelial progenitor cells during pulp wound healing process, suggesting that it is useful for vasculogenesis, dentinogenesis and pulp regeneration.

Embodiment 3

Acceleration of Dentin/Pulp Regeneration of MMP3 In Vivo Using a Rat and Dog Amputated Pulp Model 1. Application of MMP3 on a Rat Pulp Amputated Model After pulpotomy of rat upper incisor, and wash with a saline, 50 ng of MMP3 adsorbed in spongel was applied to the amputated pulp. As a control, 50 ng of MMP3 and 30 nmol NNGH adsorbed in spongel was applied to the amputated pulp. The cavity was temporally sealed with a bonding agent and a photopolymerization type composite resin (Unifil low flow, GC, Tokyo). 24 hours, 72 hours, or 7 days after application, the paraffin sections of the 5 µm thickness were examined morphologically after HE staining or Masson Trichrome staining.

For quantitative analysis of newly formed blood vessels, each 5 frozen sections at 24 hours after treatment both with MMP3 and control PBS from 4 incisors each, total 40 sections were stained with Fluorescein *Griffonia* (Bandeiraea) *Simplicifolia* lectin (BS1-lectin) as described above. Three rectangles of a standardized size (0.1 mm$^2$) were drawn in the upper part of pulp tissue under the amputated site in every five sections from one sample. The lectin-positive area relative to total area (1.5 mm$^2$) was quantitatively analyzed in a standardized procedure using BZ-II Analyzer (Keyence) software on a Keyence BZ-9000 fluorescence microscope (Keyence, Tokyo, Japan). The data were presented as means±standard deviation at 4 determinations.

To evaluate effect of MMP3 on proliferation, immunohistochemical analysis of Proliferating Cell Nuclear Antigen (PCNA) was performed. Paraffin sections of 24 hours after treatment were deparaffinized and antigen was retrieved by antigen unmasking solution (Vector Laboratories, Burlingame, Calif.) according to the manufacturer's instructions. Endogenous peroxidase activity and nonspecific staining were blocked as described earlier. The sections were incubated with anti-PCNA antibody (Dako) at dilutions of 1:100 in antibody diluent (Dako) overnight at 4° C., and further incubated with a peroxidase-conjugated secondary antibody (ImmPRESS reagent; Vector Laboratories) for 30 min at room temperature. After development by DAB Liquid System (Dako), sections were counterstained with hematoxylin, and photographed on an Olympus Vanox-s microscope (Olympus, Tokyo, Japan). For quantitative analysis of proliferating cells, each 3 paraffin sections at 24 hours after treatment both with MMP3 and control PBS from 4 incisors each were used. Three rectangles of a standardized size (0.1 mm$^2$) were drawn in the upper part of pulp tissue under the amputated site in every 3 sections. The positive staining cells were counted and quantitatively analyzed. The data were presented as means±standard deviation at 4 determinations.

For quantitative analysis of matrix formation, each 5 paraffin sections at 72 hours after treatment both with MMP3 and control PBS from 4 incisors each, and 5 sections at 7 days after treatment with MMP3, NNGH, and control PBS from 4 incisors each were stained with Masson's trichrome staining. The positive area was quantitatively analyzed in the upper part of pulp tissue under the amputated site, 2 mm in depth from the amputated site, using BZ-II Analyzer software. The data were presented as means±standard deviation at 4 determinations.

Figure 9A:
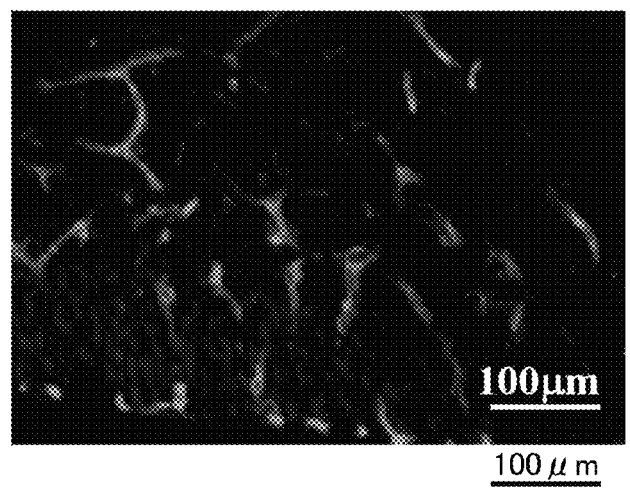
FIG. 9A is a figure of micrograph of the BS1-lectin staining 24 hours after treatment with MMP3 of amputated pulp in rat.
Figure 9B:
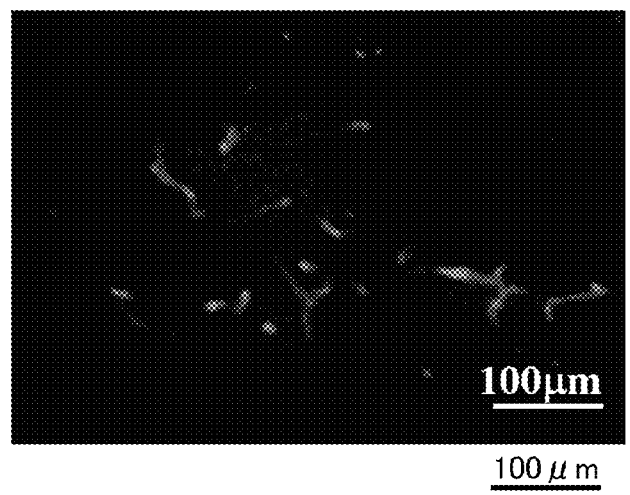
FIG. 9B is a figure of micrograph of the BS1-lectin staining 24 hours after non-treatment with MMP3 of amputated pulp in rat.

It is examined whether MMP3 induce vascularization in vivo in an injured pulp. MMP3 was applied MMP3 in the presence or absence of NNGH in rat incisor pulp. PBS was used as a negative control. FIG. 9A is a figure of BS1-lectin staining when MMP3 was applied 24 hours after pulpotomy. FIG. 9B is a figure of BS1-lectin staining when MMP3 was not applied 24 hours after pulpotomy. In the group with MMP3, a newly formed blood vessels stained with BS1-lectin was more detected under the amputated surface in comparison with an MMP3 free group 24 hours after pulpotomy.

Figure 9C:
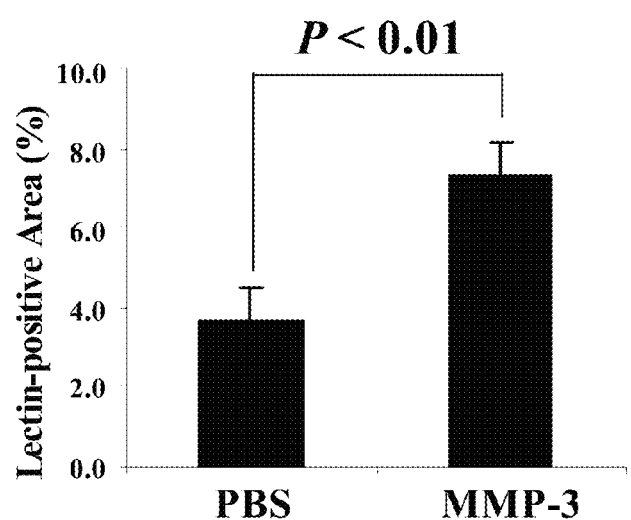
FIG. 9C is quantitative analysis indicating increased density of blood vessels induced by MMP3 in the upper part of pulp tissue under the amputated site in rat.

FIG. 9C shows the increase in density of the newly formed vessels by MMP3 in the upper part of pulp under the rat amputated pulp surface. The increase of the vascularization density was double than PBS group, and a statistically significant difference was seen in the MMP3 group as shown in FIG. 9C.

Figure 9D:
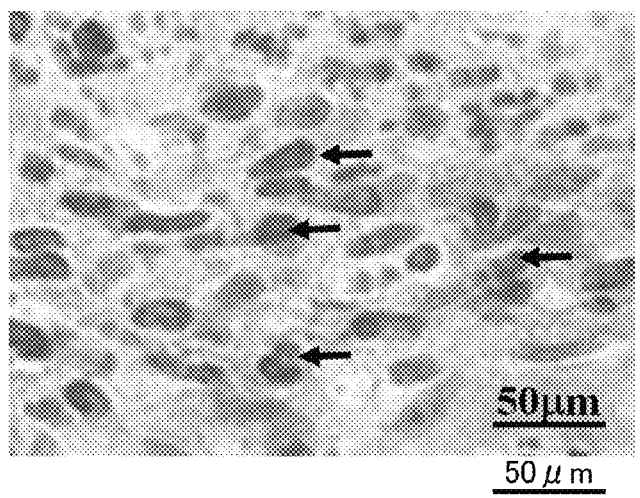
FIG. 9D is a figure of micrograph of the PCNA immunostaining 24 hours after treatment with MMP3 of amputated pulp in rat.
Figure 9E:
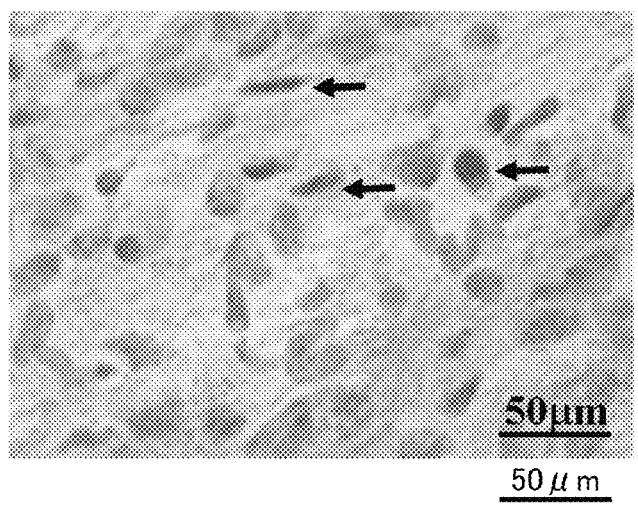
FIG. 9E is a figure of micrograph of the PCNA immunostaining 24 hours after non-treatment with MMP3 of amputated pulp in rat.

FIG. 9D is a figure of PCNA immunostaining of 24 hours after rat pulpotomy when MMP3 was applied. FIG. 9E is a figure of PCNA immunostaining of 24 hours after rat pulpotomy when MMP3 was not applied. The group which applied MMP3 was 98.5 cells/mm$^2$ ±17.7, and the group (PBS control group) which did not applied MMP3 was 36.0 cells/mm$^2$±4.1. In other words, in the group which applied MMP3, PCNA positively staining cells increased 2.7 times more frequent in the pulp under the amputated site than non applied group. The PCNA positively staining cells were observed a lot under the amputated site.

Figure 9F:
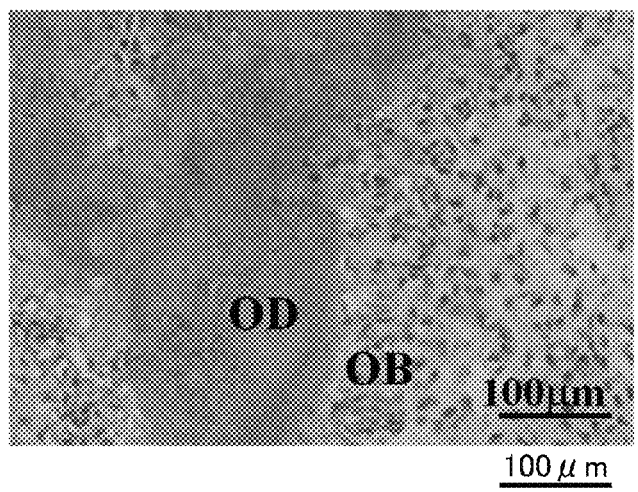
FIG. 9F is a figure of micrograph of the HE staining 72 hours after treatment with MMP3 of amputated pulp in rat.
Figure 9G:
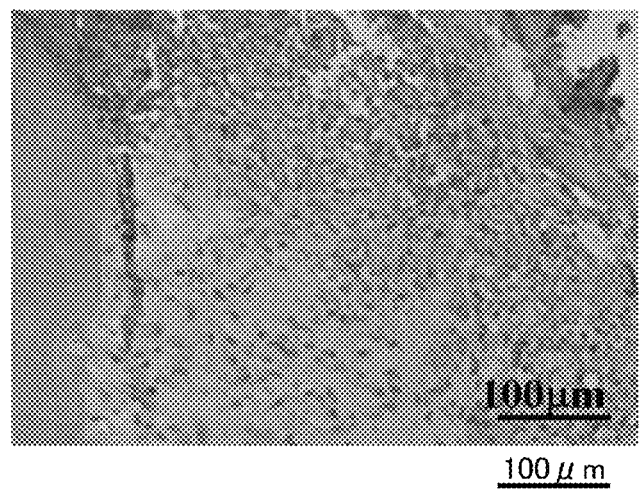
FIG. 9G is a figure of micrograph of the HE staining 72 hours after non-treatment with MMP3 of amputated pulp in rat.

FIG. 9F is a figure of HE staining of 72 hours after rat pulpotomy when MMP3 was applied. FIG. 9G is a figure of HE staining MMP3 was not applied 72 hours after rat pulpotomy. In the group with MMP3, the larger amount of osteodentin was observed in comparison with non applied MMP3. The inflammatory cell infiltration was not observed in both groups either.

Figure 9H:
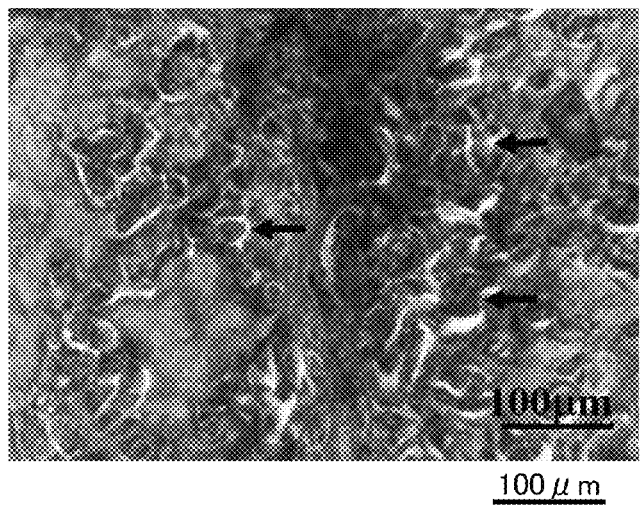
FIG. 9H is a figure of micrograph of the Masson's trichrome staining 72 hours after treatment with MMP3 of amputated pulp in rat.

FIG. 9H is a figure of Masson's Trichrome staining of 72 hours after rat pulpotomy when MMP3 was added. The osteodentin formation was observed by the Masson's Trichrome staining as shown in FIG. 9H, around the newly differentiated odontoblasts/osteodentinoblasts 72 hours after application of MMP3.

Figure 9I:
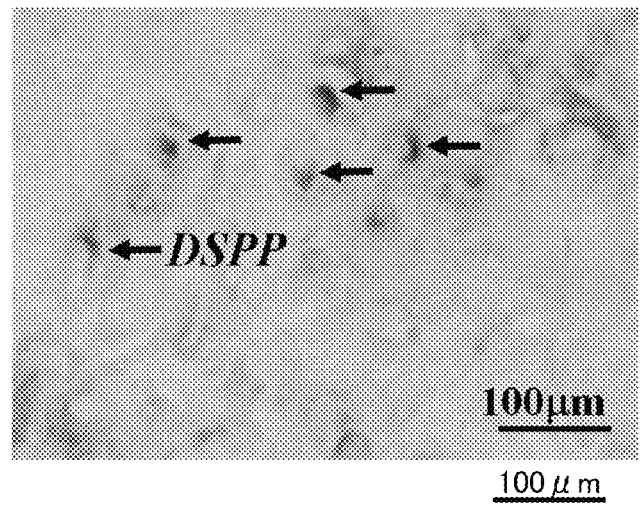
FIG. 9I is a figure of micrograph of the in situ hybridization analysis 72 hours after treatment with MMP3 of amputated pulp in rat.

FIG. 9I is in situ hybridization of 72 hours after rat pulpotomy, when MMP3 was applied, In situ hybridization analysis showed that DSPP mRNA expression was seen in the newly differentiated odontoblasts/osteodentinoblasts surrounded by a osteodentin matrix as shown in FIG. 9I.

Figure 9J:
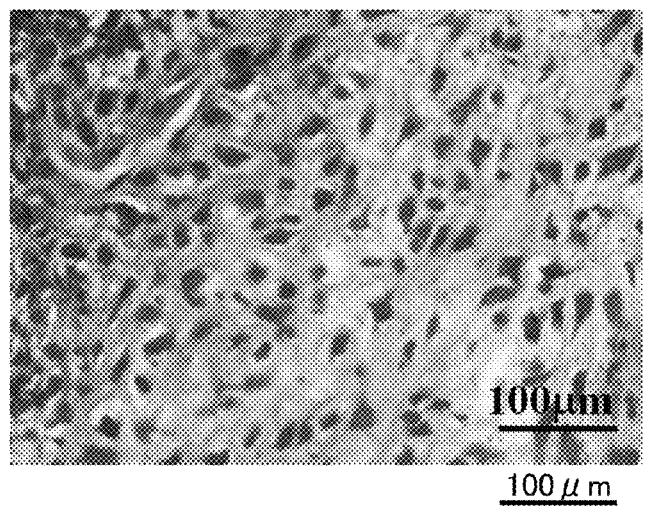
FIG. 9J is a figure of micrograph of the Masson's trichrome staining 72 hours after non-treatment with MMP3 of amputated pulp in rat.

FIG. 9J is a figure of Masson's Trichrome staining of 72 hours after rat pulpotomy when MMP3 was not applied. Odontoblasts/osteodentinoblasts was not seen in group which applied PBS and no MMP3 as shown in FIG. 9J.

Figure 9K:
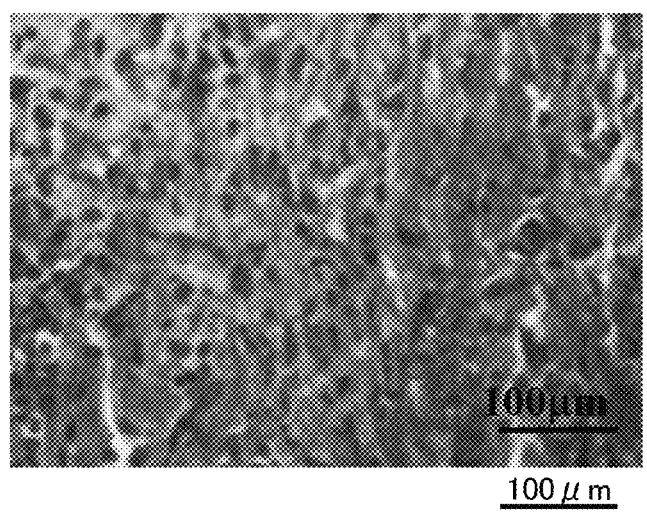
FIG. 9K is a figure of micrograph of the Masson's trichrome staining 72 hours after treatment with MMP3 and NNGH of amputated pulp in rat.

FIG. 9K is a figure of Masson's Trichrome staining of 72 hours after rat pulpotomy when MMP3 was applied with NNGH. Odontoblasts/osteodentinoblasts was not seen in the group with MMP3 and NNGH as shown in FIG. 9K.

Figure 9L:
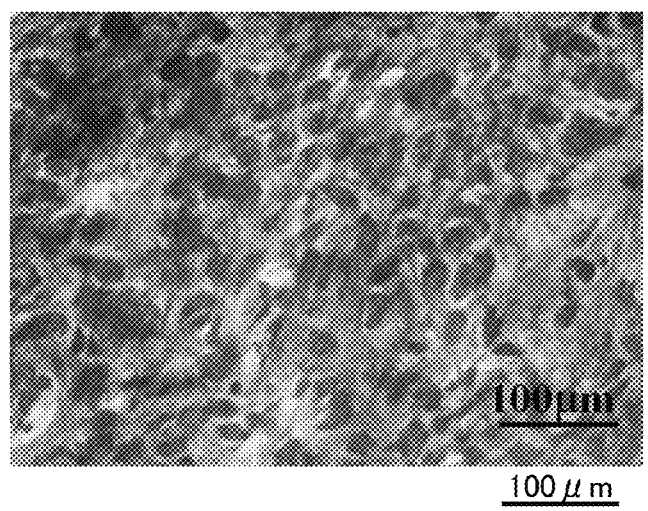
FIG. 9L is a figure of micrograph of the Masson's trichrome staining 7 days after non-treatment with MMP3 of amputated pulp in rat.

FIG. 9L is a figure of Masson's Trichrome staining when MMP3 was not applied 7 days after rat pulpotomy. In the group with PBS, odontoblasts/osteodentinoblasts was not seen as shown to FIG. 9L.

Figure 9M:
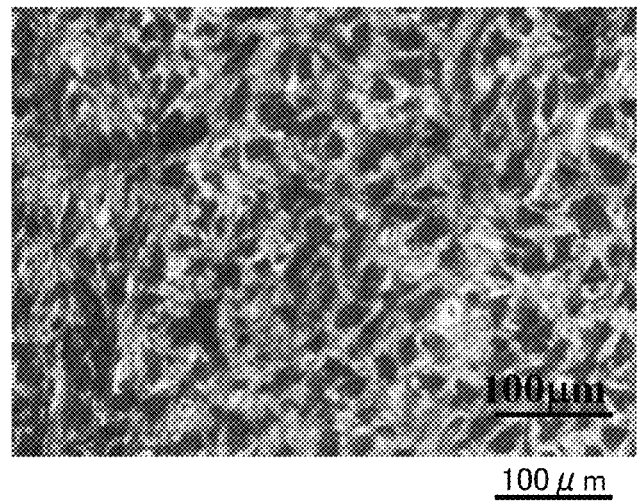
FIG. 9M is a figure of micrograph of the Masson's trichrome staining 7 days after treatment with MMP3 and NNGH of amputated pulp in rat.

FIG. 9M is a figure of Masson's Trichrome staining of 7 days after rat pulpotomy when MMP3 was applied with NNGH. Much odontoblasts/osteodentinoblasts was not seen in the group with MMP3 and NNGH as shown in FIG. 9M.

Figure 9N:
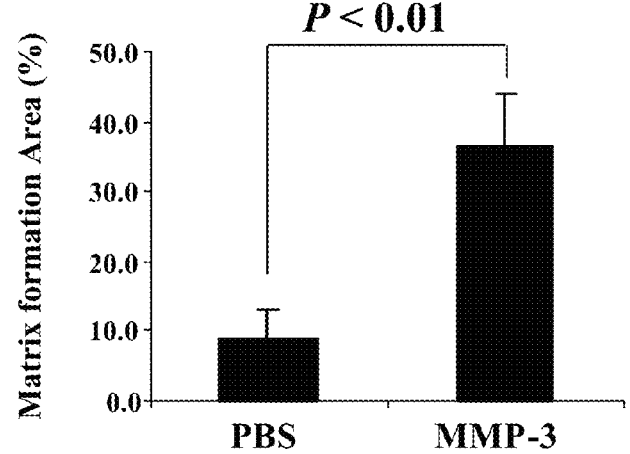
FIG. 9N is quantitative analysis indicating increased collagenous matrix formation induced by MMP3 72 hours after pulpotomy in rat.

FIG. 9N shows increase of the collagen matrix formation under the amputated site by MMP3 72 hours after rat pulpotomy. The dentin matrix formation under the amputated site 72 hours after pulpotomy, significant 3.8 times increase was seen in the group with MMP3 in comparison with PBS control group as shown in FIG. 9N (P<0.01).

Figure 9O:
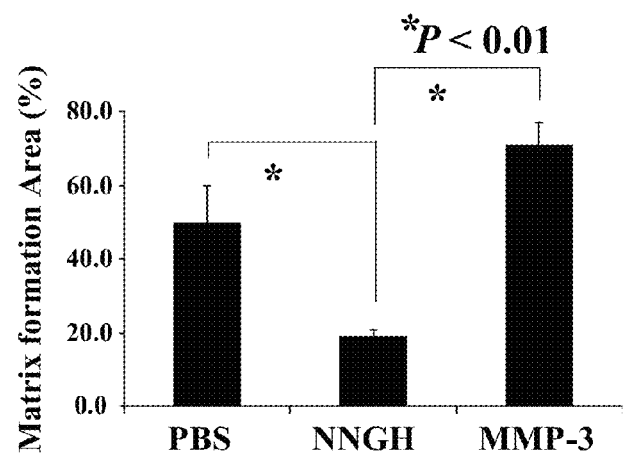
FIG. 9O is quantitative analysis indicating increased collagenous matrix formation induced by MMP3 7 days after pulpotomy in rat.

FIG. 9O shows increase of the collagen matrix formation by MMP3 7 days after rat pulpotomy. Significant decrease in the dentin matrix formation was seen in the group with NNGH in comparison with PBS control group as shown in FIG. 9O (*P<0.01).

The enhanced reparative dentin formation by MMP3 is dependent on acceleration of vascularization, and it is thought not direct enhancement of odontoblast differentiation.

2. The Application of MMP3 to a Dog Pulpotomy Model

After pulpotomy of dog upper premolar teeth, the amputated pulp was washed with 5% sodium hypochlorite solution and 3% hydrogen peroxide and further was washed with a saline, 100 ng of MMP3 absorbed in spongel was applied on the amputated pulp. Furthermore, the cavity was provisionally filled with phosphate cement and sealed with a chemical polymerization composite resin after application of a bonding agent. The tooth was extracted 14 days after treatment and fixed with 4% paraformaldehyde fixation at 4° C. overnight and decalcified at 4° C. in 10% formic acid for one week. Reparative dentin formation was observed after HE staining under light microscopy in the longitudinal paraffin 5 μm-section. Results are shown in FIGS. 10A-10E.

Figure 10A:
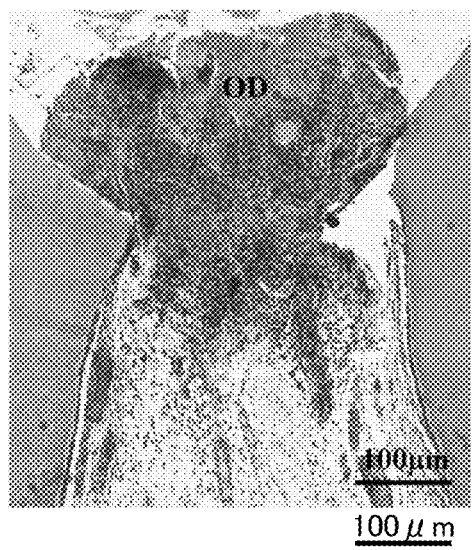
FIG. 10A is a figure of micrograph showing reparative dentin formation 14 days after treatment with MMP3 of amputated pulp in the canine upper premolar tooth.
Figure 10B:
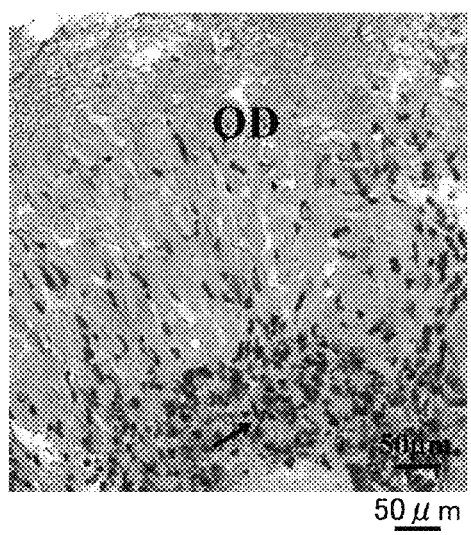
FIG. 10B is an enlarged figure of micrograph showing reparative dentin formation 14 days after treatment with MMP3 of amputated pulp in the canine upper premolar tooth.
Figure 10C:
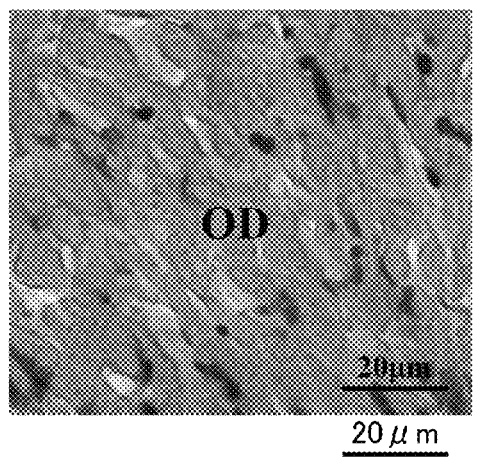
FIG. 10C is an enlarged figure of micrograph at a higher magnification showing reparative dentin formation 14 days after treatment with MMP3 of amputated pulp in the canine upper premolar tooth.
Figure 10D:
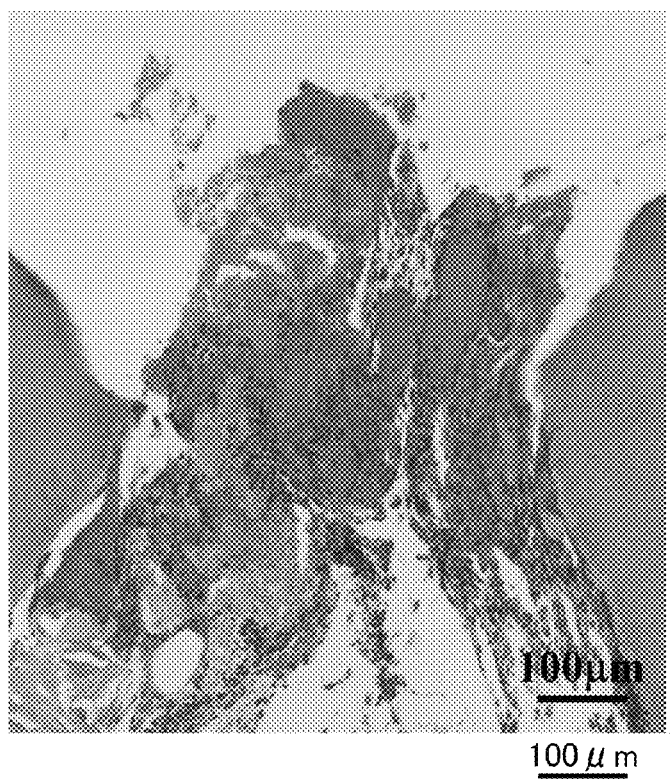
FIG. 10D is a figure of micrograph showing reparative dentin formation 14 days after treatment with PBS control of amputated pulp in the canine upper premolar tooth.
Figure 10E:
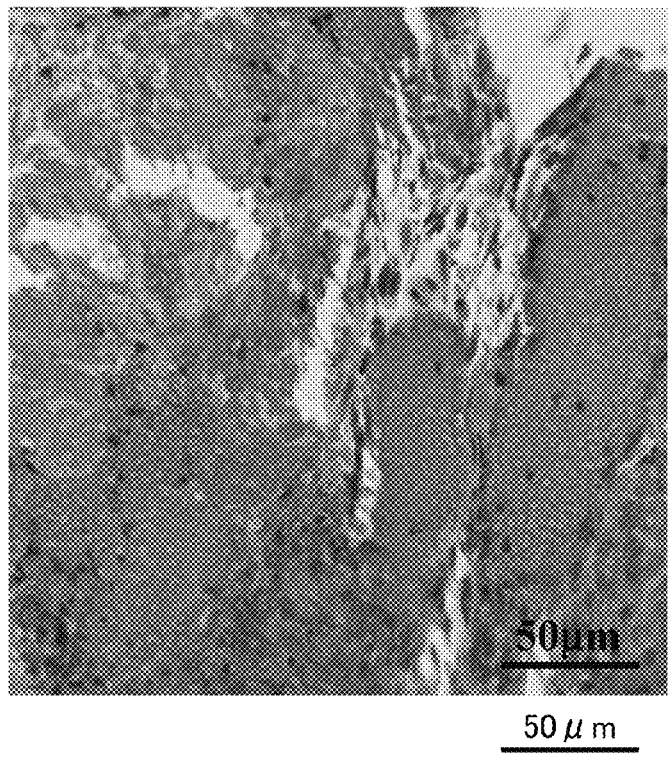
FIG. 10E is an enlarged figure of micrograph showing reparative dentin formation 14 days after treatment with PBS control of amputated pulp in the canine upper premolar tooth.

FIG. 10A is a Figure of micrograph showing the reparative dentin formation when MMP3 was applied to the upper premolar tooth of the dog 14 days after pulpotomy. The OD shows osteodentin. FIG. 10B is a figure of micrograph of the high power to show the reparative dentin formation when MMP3 was applied to the upper premolar tooth of the dog 14 days after pulpotomy. FIG. 10C is a figure of micrograph of the further high power to show the reparative dentin formation when MMP3 was applied to the upper premolar tooth of the dog 14 days after pulpotomy. FIG. 10D is a figure of micrograph in case of the PBS control to the upper premolar tooth of the dog 14 days after pulpotomy. FIG. 10E is a figure of micrograph of the high power in case of the PBS control to the upper premolar tooth of the dog 14 days after pulpotomy.

In the group with MMP3, a large number of cell proliferation was seen in the vicinity of an amputated surface as shown in FIGS. 10A-10C, and a large quantity of reparative dentin formation was seen in the upper part of the amputated pulp. However, the reparative dentin formation was not seen in the PBS control as shown in FIGS. 10D and 10E.

Embodiment 4

Dentin/Pulp Regeneration Using the Dog Pulpitis Model

Figure 11A:
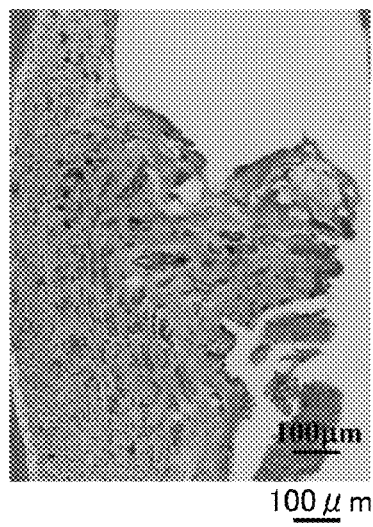
FIG. 11A is a figure of micrograph showing healing of pulp inflammation 14 days after treatment with MMP3 of pulpitis in the canine upper premolar tooth.
Figure 11B:
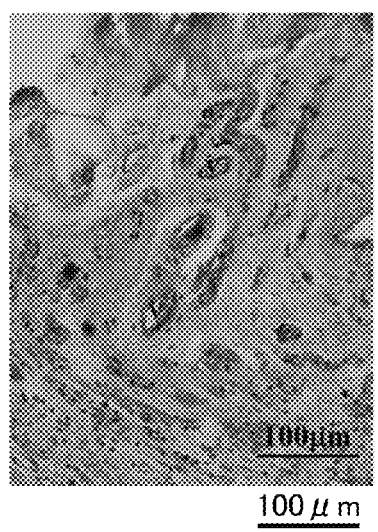
FIG. 11B is an enlarged figure of micrograph showing healing of pulp inflammation 14 days after treatment with MMP3 of pulpitis in the canine upper premolar tooth.
Figure 11C:
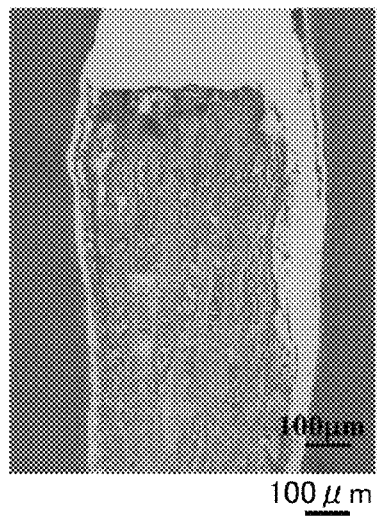
FIG. 11C is a figure of micrograph showing pulp inflammation 14 days after treatment with PBS control of pulpitis in the canine upper premolar tooth.
Figure 11D:
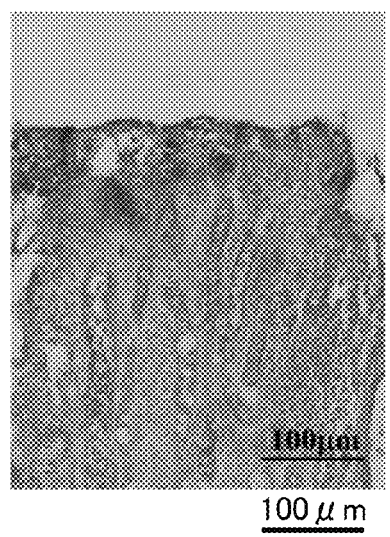
FIG. 11D is an enlarged figure of micrograph showing healing of pulp inflammation 14 days after treatment with MMP3 of pulpitis in the canine upper premolar tooth.

The inflammation of the pulp was produced be open with cotton for 24 hours after pulpotomy in the dog upper premolar tooth. Subsequently 100 ng of MMP3 absorbed in spongel was applied to the amputated pulp after washing with 5% sodium hypochlorite solution and 3% hydrogen peroxide and further with a saline. Furthermore, the cavity was filled with phosphate cement and temporally sealed with a chemical polymerization composite resin after application with a bonding agent. The tooth was extracted 14 days later, immersed at 4° C. overnight and followed by fixation and decalcification at 4° C. in 10% formic acid for one week. The reparative dentin formation was observed by an light microscope after H.E. staining at 5 μm-paraffin sections. The results were shown in FIGS. 11A-11D. FIG. 11A is a figure of micrograph showing healing of pulpitis state 14 days after MMP3 application in the upper premolar tooth of the dog in which pulpitis had been produced. FIG. 11B is a figure of micrograph of the high power to show healing of pulpitis state 14 days after MMP3 application in the upper premolar tooth of the dog in which pulpitis had been produced. FIG. 11C is a figure of micrograph 14 days in case of the PBS control of the upper premolar tooth of the dog in which pulpitis produces had been produced. FIG. 11D is a figure of micrograph of the high power 14 days in case of the PBS control of the upper premolar tooth of the dog n which pulpitis had been produced.

An inflammation state of the pulp was very slight, and proliferation was seen under the amputated pulp and vascularization was enhanced in the group with MMP3 as shown in FIGS. 11A and 11B. In addition, the reparative dentin formation was sometimes observed. However, in the case of PBS control, the healing of inflammation was not observed as shown in FIGS. 11C and 11D. Therefore, the medicaments and dental materials in this invention was shown to have anti-inflammatory sedation and vascularization, pulp regeneration when the inflammation due to the pulpitis occurred, as well as acceleration of pulp regeneration in the case of pulp injury.

Pulpal states are different between injured pulp and pulp inflammation with pulpitis. In the case of wound (the mechanical damage), the infection in the pulp tissue is not taking place, and the pulp can heal after temporal infiltration of inflammatory cells. On the other hand, the inflammation state due to the pulpitis has infection, and the immunity defense system in vivo is exercised to remove the foreign alien substance and stimulate the infiltration of the inflammatory cells (immunity charged cells) including neutrophile and macrophage depending on quality and quantity of the infection material. The blood vessel of the pulp becomes the vasodilatation state, and the permeability of the capillary is increased. When blood vessel permeability increases, a blood component goes out from the blood vessel (inflammatory infiltration), and, as a result, stromal pressure rises. Furthermore, an inflammatory mediator, protease produced by the immunity charged cells form a complicated network and cause further inflammatory exacerbation and tissue destruction. Thus, there is a difference especially in expression of inflammatory mediator between pulp injury and inflammation by pulpitis.

Embodiment 5

Odontoblastic Differentiation with Silicon Membrane with Porous Structure

Figure 12A:
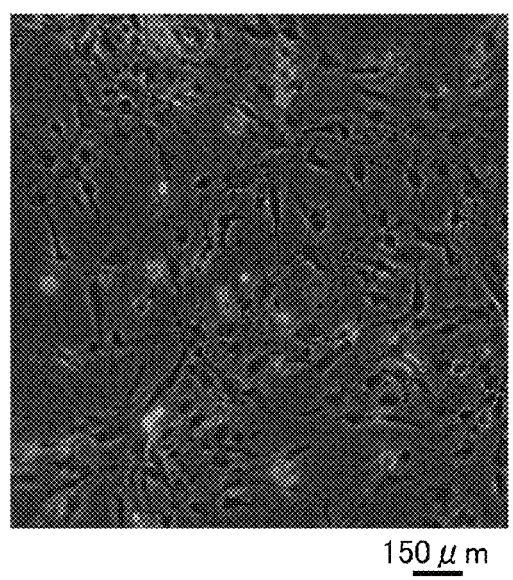
FIG. 12A is a figure of phase contrast microscope photograph 12 hours after the culture of porcine pulp CD31⁻/CD146⁻ SP cells attached to a silicon membranous carrier.

The surface of silicon membrane with high biocompatibility and oxygen permeablity was coated with plasma processing, processed to make porous structure, 7 μm in width, 7 μm in depth, 20 μm in pitch, and coated with type I collagen (cf. FIGS. 1A-1C). $CD31^{31}$/$CD146^-$ SP cells derived from pig pulp were attached on this silicon membrane at high density and cultured in Dulbecco's Modified Eagle Medium (DMEM) with 10% calf serum, 50 μg/mL ascorbic acid for 12 hours. The cell shape is shown in FIG. 12A. FIG. 12A is a figure of phase contrast microscope photograph showing $CD31^-$/$CD146^-$ SP cells attached to a silicon membrane with the recesses and cultured for 12 hours. Then, culture medium was filled in a container, and the membrane was pressed vertically from the outside with weak compression stimulation by weak pressurization movement (for six times pressurization per minute) or with strong compression stimulation by the pressurization movement (more than ten times for pressurization) for six hours in a closed system in Teflon.

In addition, pulp cells were isolated from porcine pulp using collagenase enzyme digestion method (Nakashima M. Archs oral Biol. 36 (9), 655-663, 1991). $CD31^-$/$CD146^-$ SP cells were further isolated from Side Population (SP) which strongly exhausts Hoechst 33342 using CD31 and CD146 antibody by a flow cytometer. After fractionation, plated to type I collagen coat dish and cultured in EBM2 medium with insulin-like growth factor-1 (IGF-1) and Epidermal Growth Factor (EGF) and 10% calf serum.

Figure 12B:
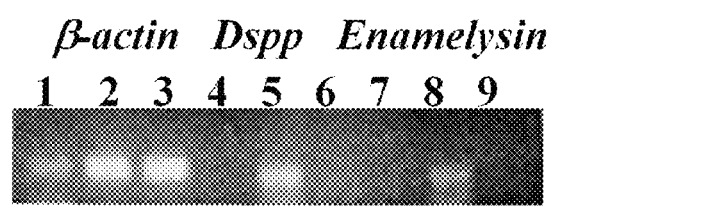
FIG. 12B is a figure showing mRNA expression of β-actin, Dspp and Enamelysin for 48 hour culture after adding perpendicular pressure on the carrier for six hours.

FIG. 12B is a figure showing mRNA expression of μ-actin, Dspp and Enamelysin two days after culture. The cells on the membrane became close contact with each other when further cultured for two days as shown in FIG. 12B, and mRNA expression such as Enamelysin and Dentin sialophosphoprotein (Dspp) was detected, indicating induction of odontoblast differentiation. The cells were induced to differentiate into odontoblasts especially with weak compression stimulation effectively.

INDUSTRIAL APPLICABILITY

This invention is applicable to recover pulp function properly even in case of pulpitis for deep caries, since it has high inflammation sedation effect. In addition, this invention is applicable to restore injured dentin precisely, since it has superior effects on vascularization, pulp regeneration and dentin formation.

DESCRIPTION OF REFERENCE CHARACTERS

100: The carrier with the recesses
110: Recesses
200: Tooth
210: Dental pulp
290: Model
300: Carrier with MMP3 protein
400: Culture device
500: Rat upper incisor tooth
510: Diamond point burr
520: Round burr
540: Section
550: Spongel
560: Resin

What is claimed is:

1. A method of treatment for pulpitis and/or enhancement for dentinogenesis in a subject in need thereof, comprising administering to the subject a dental material comprising a matrix metalloprotease 3 protein or a matrix metalioprotease 3 precursor protein as an active ingredient.

2. The method of claim 1, wherein the dental materials include a carrier having biocompatibility.

3. The method of claim 2, wherein the carrier comprises at least on one side a plurality of recesses which depth and orientation direct to a constant course, and wherein the carrier is a membranous structure consisting of materials having oxygen permeability and/or material permeability.

4. The method of claim 3, wherein the carrier comprises at least one selected from the group consisting of collagen, artificial proteoglycan, glycosaminoglycan, gelatine, hydrogel, fibrin, phosphophoryn, hyaluronic acid, chitin, glucosamine, fibronectin, alginic acid, heparan sulfate, heparin, laminin, tricalcium phosphate, hydroxyapatitte, β-TCP, polylactic acid, polyglycolic acid, poly-DL-lactic acid, lactic acid, glycolic acid copolymer, polyethylene glycol, polysilicon, polycaprolactone, calcium carbonate, titanium, gold, ceramics, silicone resin and silicon hydrogel.

5. The method of claim 2, wherein the dental materials comprises at least one of pulp cells, pulp stem cells, pulp progenitor cells, odontoblasts or cells that can differentiate into odontoblasts.

6. The method of claim 5, wherein the cells comprising at least one of pulp cells, pulp stem cells, pulp progenitor cells, odontoblasts or cells that can differentiate into odontoblasts is more than $1\times10^3$ cells/μl and lower than $1\times10^6$ cells/μl.

7. The method of claim 2, wherein the dental materials comprise epithelium.

8. The method of claim 2, wherein the dental materials comprise dentin matrix.

9. The method of claim 1, wherein the amount of the active ingredient in the dental materials is from 1 ng-100 μg, based on a dry weight of the active ingredient.

10. The method of claim 5, wherein the pulp stem cells comprise at least one of pulp SP cells, CD31-negative and CD146-negative cells, CD24-positive cells, CD105 positive cells or CD150 positive cells.

11. The method of claim 2, wherein the dental materials comprise endothelial cells or endothelial progenitor cells.

* * * * *

```
                           SEQUENCE LISTING

<160> NUMBER OF SEQ ID NOS: 24

<210> SEQ ID NO 1
   <211> LENGTH: 20
   <212> TYPE: DNA
   <213> ORGANISM: Artificial Sequence
   <220> FEATURE:
   <223> OTHER INFORMATION: oligonucleotide primer

<400> SEQUENCE: 1
aagtacccca ttgaacacgg                                              20

<210> SEQ ID NO 2
   <211> LENGTH: 20
   <212> TYPE: DNA
   <213> ORGANISM: Artificial Sequence
   <220> FEATURE:
   <223> OTHER INFORMATION: oligonucleotide primer

<400> SEQUENCE: 2
atcacaatgc cagtggtacg                                              20

<210> SEQ ID NO 3
   <211> LENGTH: 20
   <212> TYPE: DNA
   <213> ORGANISM: Artificial Sequence
   <220> FEATURE:
   <223> OTHER INFORMATION: oligonucleotide primer

<400> SEQUENCE: 3
ttgatggacc tggaggaaac                                              20

<210> SEQ ID NO 4
   <211> LENGTH: 20
   <212> TYPE: DNA
   <213> ORGANISM: Artificial Sequence
   <220> FEATURE:
   <223> OTHER INFORMATION: oligonucleotide primer

<400> SEQUENCE: 4
ggtacatcaa agccccaatg                                              20

<210> SEQ ID NO 5
   <211> LENGTH: 19
   <212> TYPE: DNA
   <213> ORGANISM: Artificial Sequence
   <220> FEATURE:
   <223> OTHER INFORMATION: oligonucleotide primer

<400> SEQUENCE: 5
gatggcaagg tgtggtgtg                                               19

<210> SEQ ID NO 6
   <211> LENGTH: 22
   <212> TYPE: DNA
```

```
<213> ORGANISM: Artificial Sequence
<220> FEATURE:
<223> OTHER INFORMATION: oligonucleotide primer

<400> SEQUENCE: 6
aatcggaagt tcttggtgta gg                                              22

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
tggcagtgaa gaagatgctg                                                 20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
gcttccctgt catcttcagc                                                 20

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 9
cgcttggata acgagttctc tc                                              22

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
gcaggaggtc ataggtcacg                                                 20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
accccactca cattctccag                                                 20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
catcgaagtg agcatctcca                                                 20
```

```
<210> SEQ ID NO 13
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 13
agtcagggtc acccacaaag                                               20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 14
ggtatccgtc catcacttgg                                               20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 15
ctacctccac catgccaagt                                               20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
acacaggacg gcttgaagat                                               20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 17
tccgtggctg acctcctctt                                               20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
cagcttcctc ggcctctggc                                               20

<210> SEQ ID NO 19
<211> LENGTH: 20
<212> TYPE: DNA
<213> ORGANISM: Artificial Sequence
<220> FEATURE:
```

```
<223> OTHER INFORMATION: oligonucleotide primer

<400> SEQUENCE: 19
gctctgcatc agtgacggta                                               20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 20
taatttcggg tcaatgcaca                                               20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 21
ggaaccgcag cacagaatga                                               20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 22
cactgttccc ctgtgcgttt                                               20

<210> SEQ ID NO 23
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 23
ggcgagatgg tggcaaga                                                 18

<210> SEQ ID NO 24
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 24
ggaagaggcg gtagttag                                                 18
```